United States Patent
Butler et al.

(10) Patent No.: US 8,518,892 B2
(45) Date of Patent: Aug. 27, 2013

(54) METHODS TO TREAT SYMPTOMS OF PATHOPHYSIOLOGY RELATED TO BODY MASS

(75) Inventors: Andrew A. Butler, Baton Rouge, LA (US); James L. Trevaskis, San Diego, CA (US)

(73) Assignee: Board of Supervisors of Louisiana State University and Agricultural Mechanical College, Baton Rouge, LA (US)

( * ) Notice: Subject to any disclaimer, the term of this patent is extended or adjusted under 35 U.S.C. 154(b) by 125 days.

(21) Appl. No.: 12/848,308

(22) Filed: Aug. 2, 2010

(65) Prior Publication Data

US 2010/0299769 A1    Nov. 25, 2010

Related U.S. Application Data

(63) Continuation of application No. 12/012,627, filed on Feb. 5, 2008, now abandoned, which is a continuation-in-part of application No. PCT/US2006/030686, filed on Aug. 7, 2006.

(60) Provisional application No. 60/705,940, filed on Aug. 5, 2005.

(51) Int. Cl.
*A61K 38/00* (2006.01)
*A61K 38/17* (2006.01)
*A61K 38/18* (2006.01)

(52) U.S. Cl.
USPC ............. 514/21.3; 514/4.8; 514/5.8; 514/6.8; 514/7.4

(58) Field of Classification Search
None
See application file for complete search history.

(56) References Cited

U.S. PATENT DOCUMENTS 7,344,861 B2   3/2008   Jacobs et al.
2003/0096951 A1   5/2003   Jacobs et al.

FOREIGN PATENT DOCUMENTS

WO   WO 00/09552 A1   2/2000
WO   WO 02/070539 A2   9/2002

OTHER PUBLICATIONS

Bork et al., "Go hunting in sequence databases but watch out for the traps", Trends in Genetics, 12(10): 425-427 (1996).
Bork, "Powers and Pitfalls in Sequence Analysis: The 70% Hurdle", Genome Research, 10: 398-400 (2000).
Brenner, "Errors in genome annotation", Trends in Genetics, 15: 132-133 (1999).
Butler et al., "A unique metabolic syndrome causes obesity in the melanocortin-3 receptor-deficient mouse", Endocrinology, 141: 3518-3521 (2000).
Clark et al., "The secreted protein discovery initiative (SDPI), a large-scale effort to identify novel human secreted and transmembrane proteins: A bioinformatics assessment", Genome Res., 13: 2265-2270 (2003).
Flier, J.S., "Obesity wars: molecular progress confronts an expanding epidemic", Cell, 116: 337-350 (2004).
Marks, D.L., "Differential roles of melanocortin receptor subtypes in cachexia", Endocrinology, 144: 1513-1523 (2003).
Ngo et al., The Protein Folding Problem and Tertiary Structure Prediction, Merz et al., eds., Birkhauser, Boston, pp. 492-495 (1994).
Asilmaz, E. et al., "Site and mechanism of leptin action in a rodent form of congenital lipodystrophy," J Clin Invest, vol. 113, pp. 414-424 (2004).
Chen, G. et al., "Disappearance of body fat in normal rats induced by adenovirus-mediated leptin gene therapy," Proc Natl Acad Sci U S A, vol. 93, pp. 14795-14799 (1996).
Minokoshi, Y. et al., "Leptin stimulates fatty-acid oxidation by activating AMP-activated protein kinase," Nature, vol. 415, pp. 339-343 (2002).
Nishizawa, H. et al., "Musclin, a novel skeletal muscle-derived secretory factor," J Biol Chem, vol. 279, pp. 19391-19395 (2004).
Ogawa, Y. et al., "Increased glucose metabolism and insulin sensitivity in transgenic skinny mice overexpressing leptin," Diabetes, vol. 48, pp. 1822-1829 (1999).
Oike, Y. et al., "Angiopoietin-related growth factor antagonizes obesity and insulin resistance," Nat Med, vol. 11, pp. 400-408 (2005).
Satoh, H. et al. "Adenovirus-mediated chronic "hyper-resistinemia" leads to in vivo insulin resistance in normal rats," J Clin Invest, vol. 114, pp. 224-231 (2004).
Yamauchi, T. et al., "Globular adiponectin protected ob/ob mice from diabetes and ApoE-deficient mice from atherosclerosis," J Biol Chem, vol. 278, pp. 2461-2468 (2003).

*Primary Examiner* — Christine J Saoud
(74) *Attorney, Agent, or Firm* — Bonnie J. Davis; John H. Runnels

(57) ABSTRACT

The expression of a mRNA encoding a putative 76 amino acid, secreted protein ("Enho1") was found to negatively correlate with fasting triglyceride and cholesterol levels. A recombinant adenovirus was used to increase the expression of Enho1 mRNA in two mouse models of obesity, KK-A$^y$ and Lep$^{ob}$/Lep$^{ob}$ mice. Over-expression of Enho1 by adenovirus injection significantly, and reproducibly, reduced fasting triglyceride and cholesterol levels in both models. In addition, transgenic mice strains were made that over express Enho1 protein. Additionally, the expression of a key gene involved in lipogenesis (fatty acid synthase) and FAS protein levels were reduced by ENHO1 adenoviral treatment in Lep$^{ob}$/Lep$^{ob}$ mice. Full-length ENHO1 peptide, or peptide derivatives, homologues, analogues, or mimetics thereof, delivered by oral intake, injection, subcutaneous patch, or intranasal routes, could be used as therapeutic or diagnostic agents for hypercholesterolemia, hypertriglyceridemia, insulin resistance, obesity, diabetes, and/or energy imbalance.

3 Claims, 14 Drawing Sheets

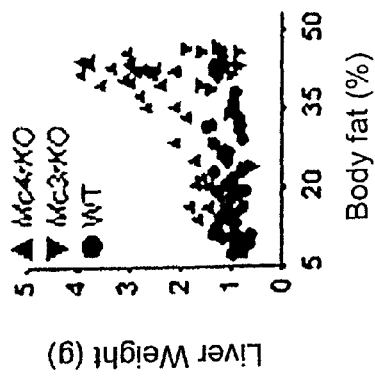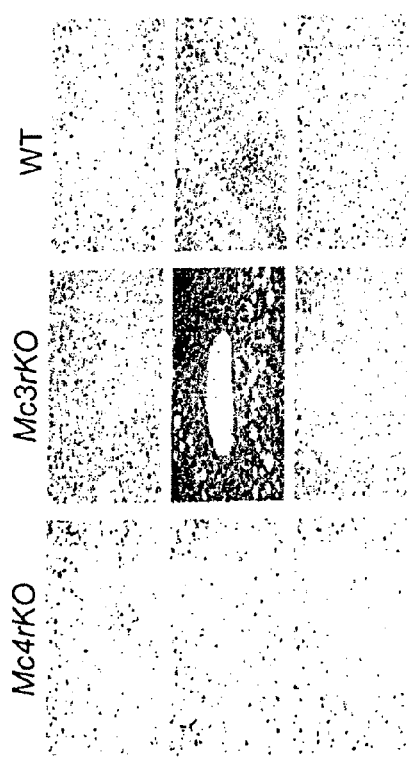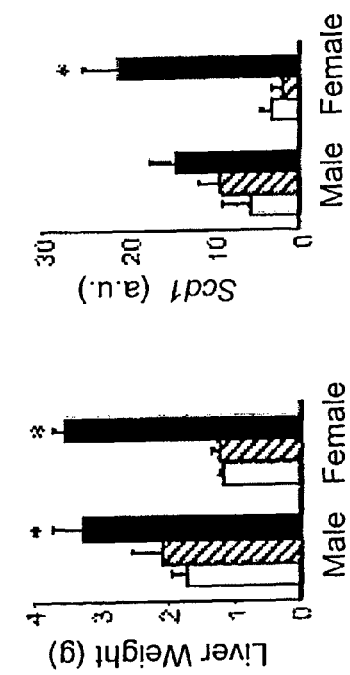
Fig. 2A
Fig. 2B
Fig. 2C
Fig. 2D
Fig. 2E

Fig. 4

|            | pAB1                                                                                  | pAB2                                      |
|------------|---------------------------------------------------------------------------------------|-------------------------------------------|

```
                                            pAB1                                                              pAB2
Mouse       MGAAISQGALIAIVCNGLVGFLLLLLWVILCWACHSRSADVDSLSESSPNSSPGPCPEKAPPPQKPSHEGSYLLQP
Rat         MGAAISQGALIAIVCNGLVGFLLLLLWVILCWACHSRSADVDSLSESSPNSSPGPCPEKAPPPQKPSHEGSYLLQP
Chimpanzee  MGAAISQGALIAIVCNGLVGFLLLLLWVILCWACHSRSADVDSLSESSPNSSPGPCPEKAPPPQKPSHEGSYLLQP
Human       MGAAISQGALIAIVCNGLVGFLLLLLWVILCWACHSRSADVDSLSESSPNSSPGPCPEKAPPPQKPSHEGSYLLQP
Dog         MGAAISQGALIAIVCNGLVGFLLLLLWVILCWACHSRSADIDSLSESSPNSSPGPCPEKAPPPQKPSHEGSYLLQP
Pig         MGAAISQGALIAIICNGLVGFLLLLLWVILCWACHSRSANIDSLSESSPNSSPGPCPEKAPPPQKPSHEGSYLLQP
Cow         MGAALSQGALIAIICNGLVGFLLLLLWVILCWACHSRSANIDSLSESSPNSSPGPCPEKAPPPQKPSHEGSYLLQP
Sheep       MGAALSQGALIAIICNGLVGFLLLLLWVILCWACHSRSANIDSLSESSPNSSPGPCPEKAPPPQKPSHEGSYLLQP
```

Fig. 5

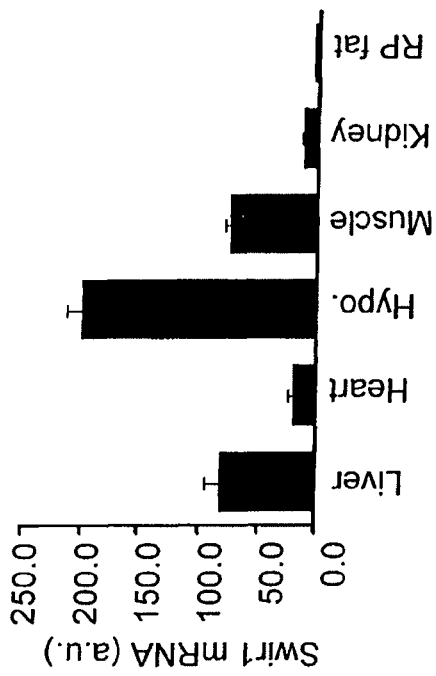
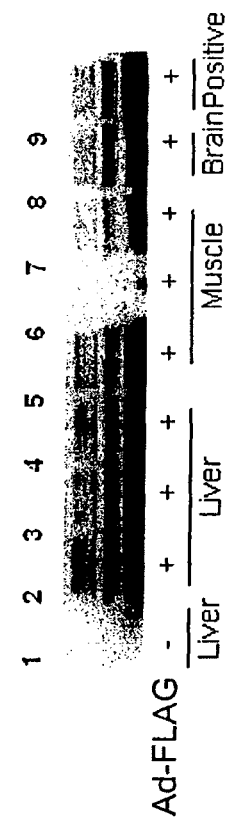
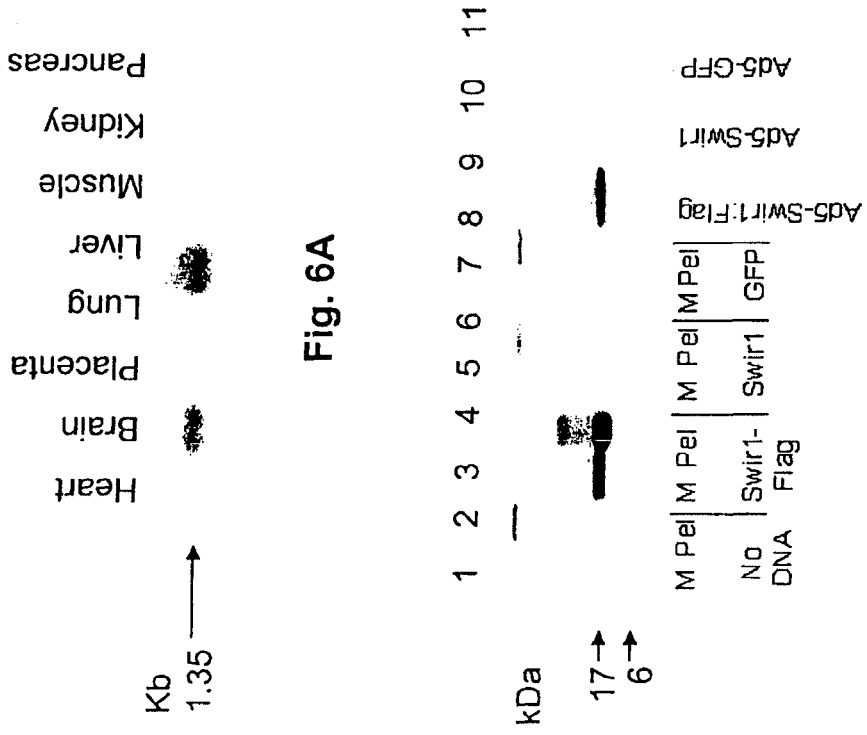
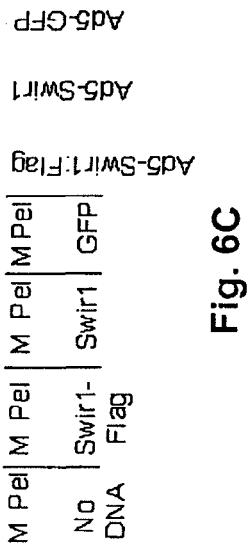
Fig. 6A
Fig. 6B
Fig. 6C
Fig. 6D

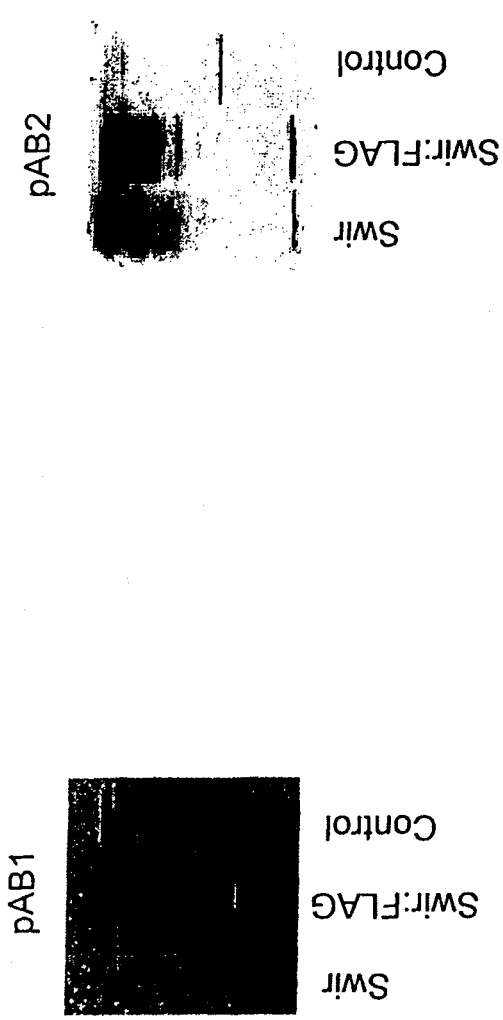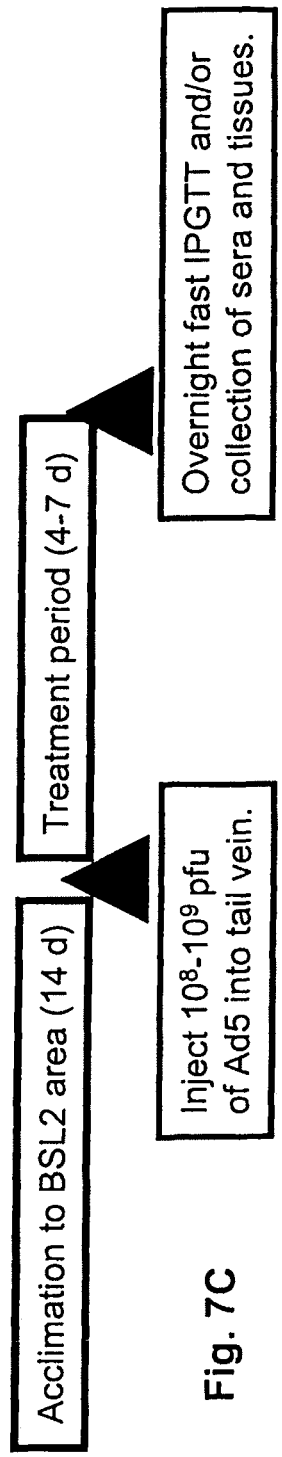

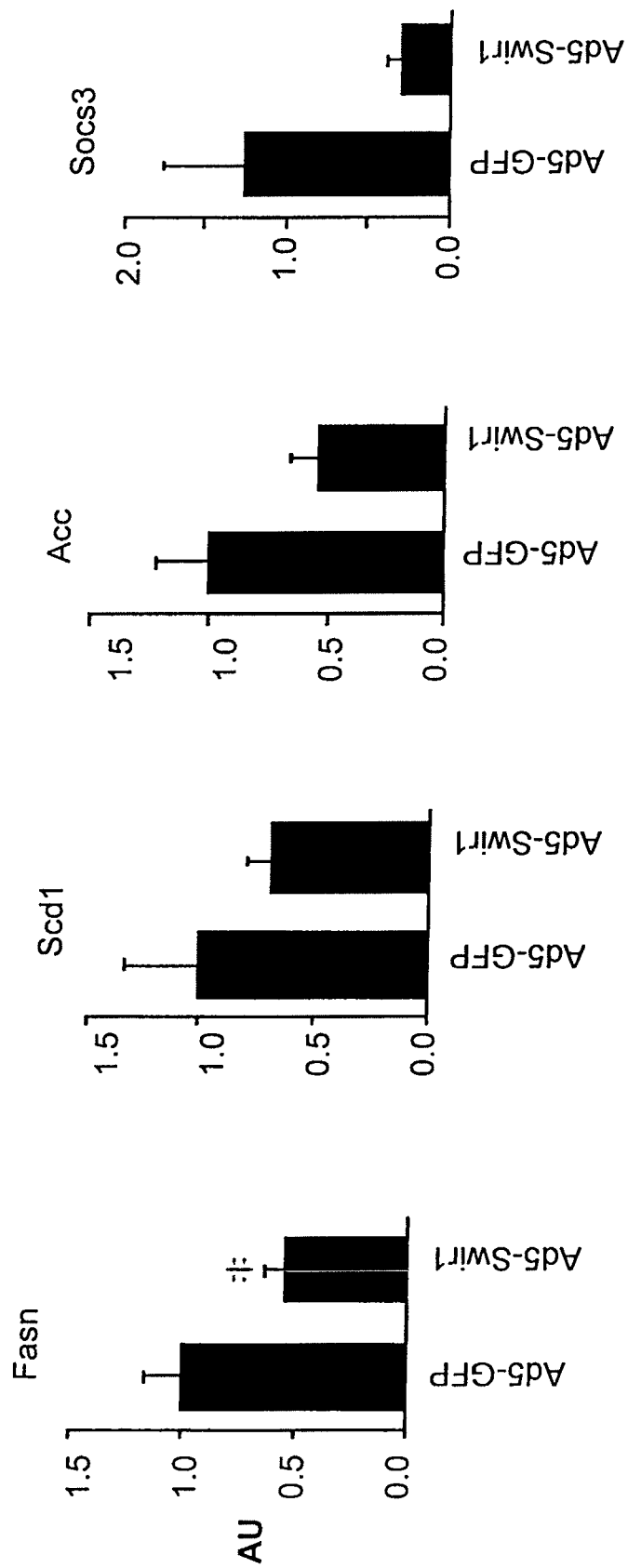

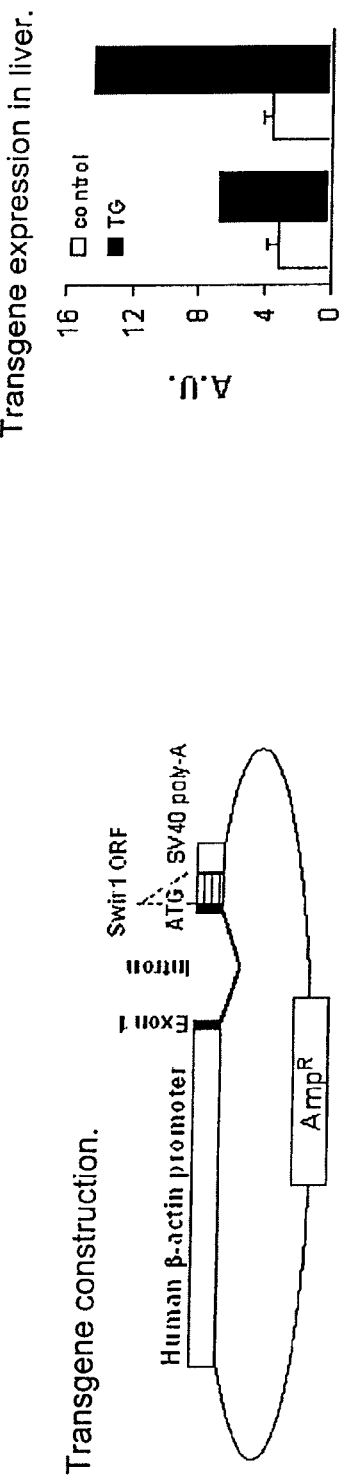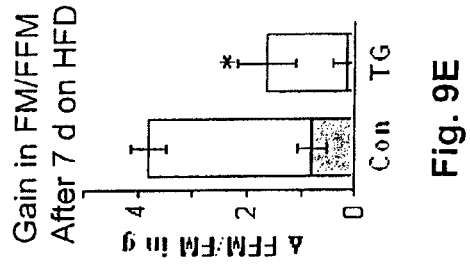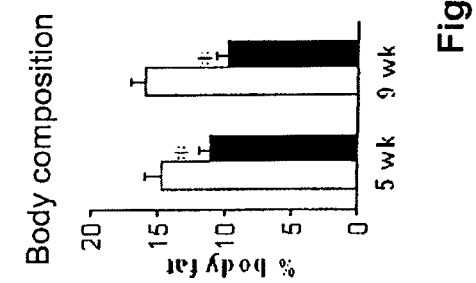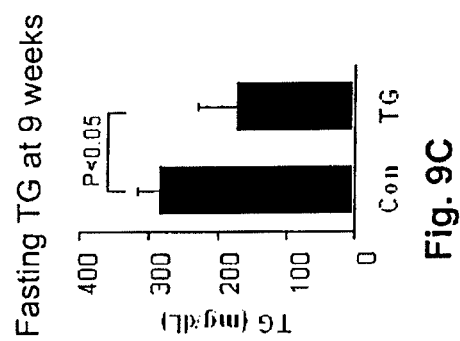

Increased metabolic rate (VO2) and whole body fat oxidation (lower RER) in BAP-Swirl1 transgenic mice.

SEQUENCE LISTING

```
<160> NUMBER OF SEQ ID NOS: 18

<210> SEQ ID NO 1
<211> LENGTH: 868
<212> TYPE: DNA
<213> ORGANISM: mus sp.

<400> SEQUENCE: 1
cccgttgtcc cggaccctct cgcgggcgcg caccggctc  aactcaggcc caggactgca      60
ggtgggcatc ttccctgcca agaagtcgct gtgtgtggac aggacagcca ccttggatgg     120
ttggccaccc cagagttgtg cctcggcatg ggccttgccg ctgaggcagc tccactgtct     180
gcgctggcct gagggtgctg tctgtcatgg gggcagccat ctcccaaggg gctctcatcg     240
ccatcgtctg caatggcctc gtaggcttct tgctgctact gctctgggtc attctctgct     300
gggcctgcca ttctcgatct gctgacgtcg attctctctc ggaatccagt cccaactcca     360
gccctggccc ctgtcctgag aaggcgccac caccccagaa gcccagccat gaaggcagct     420
acctgctgca gccctgaagg gctctggcct agcctggagt cctggacctg agtatacctg     480
agtcagagcg tggaatcgga tccaagaagt cagtcggcct ggggtccagt cgatttgaca     540
ctggacccag cagcctagat tgtagccagc ctggctccaa gagaggcctg agtggccctta    600 gagagaaagg cctggagggg gggttaggag ttggtgctag ggccagggcc atctggactc     660
tgctccatcc caagggccaa gggctgagtc catgccttcc ctaggctcag cacatctggg     720
ctccctaggt tggggagcaa acgggaaccc catggcaata atgggagggt gtccaggctg     780
ggccccttct ctggtcctcc cactgtttgt tgggtaataa atgggactat ggcttgcaaa     840
aaaaaaaaaa aaaaaaaaaa aaaaaaaa                                         868

<210> SEQ ID NO 2
<211> LENGTH: 76
<212> TYPE: PRT
<213> ORGANISM: mus sp.

<400> SEQUENCE: 2

Met Gly Ala Ala Ile Ser Gln Gly Ala Leu Ile Ala Ile Val Cys Asn
1               5                   10                  15

Gly Leu Val Gly Phe Leu Leu Leu Leu Trp Val Ile Leu Cys Trp
            20                  25                  30
```

```
Ala Cys His Ser Arg Ser Ala Asp Val Asp Ser Leu Ser Glu Ser Ser
        35                  40                  45

Pro Asn Ser Ser Pro Gly Pro Cys Pro Glu Lys Ala Pro Pro Pro Gln
    50                  55                  60

Lys Pro Ser His Glu Gly Ser Tyr Leu Leu Gln Pro
65                  70                  75

<210> SEQ ID NO 3
<211> LENGTH: 22
<212> TYPE: DNA
<213> ORGANISM: Artificial sequence
<220> FEATURE:
<223> OTHER INFORMATION: Synthetic primer

<400> SEQUENCE: 3
cctgagggtg ctgtctgtca tg                                          22

<210> SEQ ID NO 4
<211> LENGTH: 22
<212> TYPE: DNA
<213> ORGANISM: Artificial sequence
<220> FEATURE:
<223> OTHER INFORMATION: Synthetic primer

<400> SEQUENCE: 4
cagtagcagc aagaagccta cg                                          22

<210> SEQ ID NO 5
<211> LENGTH: 21
<212> TYPE: DNA
<213> ORGANISM: Artificial sequence
<220> FEATURE:
<223> OTHER INFORMATION: Synthetic primer

<400> SEQUENCE: 5
ctctcatcgc catcgtctgc a                                           21

<210> SEQ ID NO 6
<211> LENGTH: 35
<212> TYPE: DNA
<213> ORGANISM: Artificial sequence
<220> FEATURE:
<223> OTHER INFORMATION: Synthetic primer

<400> SEQUENCE: 6
ggggcggccg caccatgggg gcagccatct cccaa                            35

<210> SEQ ID NO 7
<211> LENGTH: 33
<212> TYPE: DNA
<213> ORGANISM: Artificial sequence
<220> FEATURE:
<223> OTHER INFORMATION: Synthetic primer

<400> SEQUENCE: 7
gggctcgagg gccagagccc ttcagggctg cag                              33

<210> SEQ ID NO 8
<211> LENGTH: 14
<212> TYPE: PRT
<213> ORGANISM: Mus sp.

<400> SEQUENCE: 8

Cys His Ser Arg Ser Ala Asp Val Asp Ser Leu Ser Glu Ser
1               5                   10
```

```
<210> SEQ ID NO 9
<211> LENGTH: 16
<212> TYPE: PRT
<213> ORGANISM: mus sp.

<400> SEQUENCE: 9

Pro Pro Pro Gln Lys Pro Ser His Glu Gly Ser Tyr Leu Leu Gln Pro
1               5                   10                  15

<210> SEQ ID NO 10
<211> LENGTH: 43
<212> TYPE: PRT
<213> ORGANISM: mus sp.

<400> SEQUENCE: 10

Cys His Ser Arg Ser Ala Asp Val Asp Ser Leu Ser Glu Ser Ser Pro
1               5                   10                  15

Asn Ser Ser Pro Gly Pro Cys Pro Glu Lys Ala Pro Pro Gln Lys
            20                  25                  30

Pro Ser His Glu Gly Ser Tyr Leu Leu Gln Pro
        35                  40

<210> SEQ ID NO 11
<211> LENGTH: 38
<212> TYPE: PRT
<213> ORGANISM: mus sp.

<400> SEQUENCE: 11

Ala Asp Val Asp Ser Leu Ser Glu Ser Ser Pro Asn Ser Ser Pro Gly
1               5                   10                  15

Pro Cys Pro Glu Lys Ala Pro Pro Gln Lys Pro Ser His Glu Gly
            20                  25                  30

Ser Tyr Leu Leu Gln Pro
        35

<210> SEQ ID NO 12
<211> LENGTH: 76
<212> TYPE: PRT
<213> ORGANISM: Rattus rattus

<400> SEQUENCE: 12

Met Gly Ala Ala Ile Ser Gln Gly Ala Leu Ile Ala Ile Val Cys Asn
1               5                   10                  15

Gly Leu Val Gly Phe Leu Leu Leu Leu Trp Val Ile Leu Cys Trp
            20                  25                  30

Ala Cys His Ser Arg Ser Ala Asp Val Asp Ser Leu Ser Glu Ser Ser
            35                  40                  45

Pro Asn Ser Ser Pro Gly Pro Cys Pro Glu Lys Ala Pro Pro Gln
        50                  55                  60

Lys Pro Ser His Glu Gly Ser Tyr Leu Leu Gln Pro
65                  70                  75

<210> SEQ ID NO 13
<211> LENGTH: 76
<212> TYPE: PRT
<213> ORGANISM: Pan troglodytes

<400> SEQUENCE: 13

Met Gly Ala Ala Ile Ser Gln Gly Ala Leu Ile Ala Ile Val Cys Asn
1               5                   10                  15

Gly Leu Val Gly Phe Leu Leu Leu Leu Leu Trp Val Ile Leu Cys Trp
```

```
                    20                  25                  30

Ala Cys His Ser Arg Ser Ala Asp Val Asp Ser Leu Ser Glu Ser Ser
                35                  40                  45

Pro Asn Ser Ser Pro Gly Pro Cys Pro Glu Lys Ala Pro Pro Pro Gln
            50                  55                  60

Lys Pro Ser His Glu Gly Ser Tyr Leu Leu Gln Pro
65                  70                  75

<210> SEQ ID NO 14
<211> LENGTH: 76
<212> TYPE: PRT
<213> ORGANISM: Homo sapiens

<400> SEQUENCE: 14

Met Gly Ala Ala Ile Ser Gln Gly Ala Leu Ile Ala Ile Val Cys Asn
1               5                   10                  15

Gly Leu Val Gly Phe Leu Leu Leu Leu Trp Val Ile Leu Cys Trp
                20                  25                  30

Ala Cys His Ser Arg Ser Ala Asp Val Asp Ser Leu Ser Glu Ser Ser
                35                  40                  45

Pro Asn Ser Ser Pro Gly Pro Cys Pro Glu Lys Ala Pro Pro Pro Gln
            50                  55                  60

Lys Pro Ser His Glu Gly Ser Tyr Leu Leu Gln Pro
65                  70                  75

<210> SEQ ID NO 15
<211> LENGTH: 76
<212> TYPE: PRT
<213> ORGANISM: Canis familiaris

<400> SEQUENCE: 15

Met Gly Ala Ala Ile Ser Gln Gly Ala Leu Ile Ala Ile Val Cys Asn
1               5                   10                  15

Gly Leu Val Gly Phe Leu Leu Leu Leu Trp Val Ile Leu Cys Trp
                20                  25                  30

Ala Cys His Ser Arg Ser Ala Asp Ile Asp Ser Leu Ser Glu Ser Ser
                35                  40                  45

Pro Asn Ser Ser Pro Gly Pro Cys Pro Glu Lys Ala Pro Pro Pro Gln
            50                  55                  60

Lys Pro Ser His Glu Gly Ser Tyr Leu Leu Gln Pro
65                  70                  75

<210> SEQ ID NO 16
<211> LENGTH: 76
<212> TYPE: PRT
<213> ORGANISM: Sus sp.

<400> SEQUENCE: 16

Met Gly Ala Ala Ile Ser Gln Gly Ala Leu Ile Ala Ile Ile Cys Asn
1               5                   10                  15

Gly Leu Val Gly Phe Leu Leu Leu Leu Trp Val Ile Leu Cys Trp
                20                  25                  30

Ala Cys His Ser Arg Ser Ala Asn Ile Asp Ser Leu Ser Glu Ser Ser
                35                  40                  45

Pro Asn Ser Ser Pro Gly Pro Cys Pro Glu Lys Ala Pro Pro Pro Gln
            50                  55                  60

Lys Pro Ser His Glu Gly Ser Tyr Leu Leu Gln Pro
65                  70                  75
```

```
<210> SEQ ID NO 17
<211> LENGTH: 76
<212> TYPE: PRT
<213> ORGANISM: Bovidae

<400> SEQUENCE: 17

Met Gly Ala Ala Leu Ser Gln Gly Ala Leu Ile Ala Ile Ile Cys Asn
1               5                   10                  15

Gly Leu Val Gly Phe Leu Leu Leu Leu Trp Val Ile Leu Cys Trp
            20                  25                  30

Ala Cys His Ser Arg Ser Ala Asn Ile Asp Ser Leu Ser Glu Ser Ser
            35                  40                  45

Pro Asn Ser Ser Pro Gly Pro Cys Pro Glu Lys Ala Pro Pro Pro Gln
        50                  55                  60

Lys Pro Ser His Glu Gly Ser Tyr Leu Leu Gln Pro
65                  70                  75

<210> SEQ ID NO 18
<211> LENGTH: 76
<212> TYPE: PRT
<213> ORGANISM: Ovis aries

<400> SEQUENCE: 18

Met Gly Ala Ala Leu Ser Gln Gly Ala Leu Ile Ala Ile Ile Cys Asn
1               5                   10                  15

Gly Leu Val Gly Phe Leu Leu Leu Leu Trp Val Ile Leu Cys Trp
            20                  25                  30

Ala Cys His Ser Arg Ser Ala Asn Ile Asp Ser Leu Ser Glu Ser Ser
            35                  40                  45

Pro Asn Ser Ser Pro Gly Pro Cys Pro Glu Lys Ala Pro Pro Pro Gln
        50                  55                  60

Lys Pro Ser His Glu Gly Ser Tyr Leu Leu Gln Pro
65                  70                  75
```

METHODS TO TREAT SYMPTOMS OF PATHOPHYSIOLOGY RELATED TO BODY MASS

This application is a continuation of U.S. application Ser. No. 12/012,627, filed Feb. 5, 2008, now abandoned which application is a continuation-in-part of expired international (PCT) application No. PCT/US20006/030686, filed Aug. 7, 2006, designating the United States, which application claims priority to U.S. provisional application 60/705,940 filed Aug. 5, 2005.

TECHNICAL FIELD

This invention pertains to a novel gene and resulting protein, named "Energy Homeostasis Associated-1" (Enho1) which was found to be involved in the association of obesity with insulin resistance and lipidemia.

BACKGROUND ART

Obesity is an increasingly prevalent global disease and has reached epidemic proportions. Current estimates suggest that at least 50% of the Western population is either overweight or obese. Obesity, particularly abdominal obesity, combined with other conditions such as insulin resistance, dyslipidemia, hepatic steatosis, and hypertension is known as the Metabolic, or Insulin Resistance, Syndrome. The central pathophysiological features of the dyslipidemia associated with insulin resistance and type 2 diabetes are increased plasma triglycerides (TG) in very low density lipoproteins (VLDL), and reduced high density lipoprotein (HDL) cholesterol. Commonly, increased circulating TGs are hydrolyzed into free fatty acids (FFA) and are taken up by peripheral tissues including the liver and can lead to hepatic steatosis, or non-alcoholic fatty liver. Studies of several mutant mouse models of obesity and metabolic disorders suggest that the link between insulin resistance and dysregulated TG is complex and involves both peripheral and central factors.

Insulin resistance refers to reduced insulin-stimulated glucose uptake in skeletal muscle and fat, and an impaired suppression of liver glucose output (2). Hyperglycemia and hyperlipidemia are both side effects of, and causative agents in, the pathophysiology of type 2 diabetes. Glucotoxicity and lipotoxicity further promote insulin resistance and type 2 diabetes due to suppression of insulin action and secretion from the β-cell. Hyperinsulinemia is initially successful in suppressing liver glucose output, however the deleterious effects of increased insulin offset the gains associated with maintaining normal blood glucose levels (2). Hyperinsulinemia is thought to be a factor in a cluster of metabolic abnormalities, including hypertension, non-alcoholic fatty liver disease (NAFLD) and coronary heart disease (2). NAFLD disease is commonly associated with insulin resistance, and requires two transcription factors: sterol regulatory element binding protein-1c (SREBP1c) and peroxisome proliferator receptor-γ (PPARγ) (3-6). Absence of SREBP1, or PPARγ signaling in liver inhibits the development of liver steatosis that occurs in obese insulin resistant mice (5-7).

Defining a common mechanism explaining insulin resistance has been difficult because of the complexity of the insulin receptor (IR) signaling system, and the realization that it is not one, but many factors that contribute to the development of this disorder. The tyrosine phosphorylation of two adaptor proteins, IRS1 and IRS2, is a critical early step in the stimulation of glucose uptake by insulin (8-11). IRS1 and IRS2 have no intrinsic enzymatic activity, and are thought to function as part of a molecular scaffold that facilitates the formation of complexes of proteins with kinase, phosphatase or ubiquitin ligase function (12). Stimulation of phosphoinositide 3' kinase (PI3K) by association with the IRS is a critical step in insulin-stimulated glucose uptake. Activation of the p110 catalytic subunit of PI3K activates the lipid kinase domain, which phosphorylates phosphatidylinositol-4,5-bisphosphate. Activation of PI3K is necessary for full stimulation of glucose uptake by insulin, although other pathways might also be involved (12).

A metabolic state conducive to the development of insulin resistance is thought to result from an imbalance of caloric intake with oxidative metabolism (13,14). Studies suggest that reduced mitochondrial function in muscle is a factor in the development of insulin resistance associated with obesity (14,15). Stimulation of energy expenditure and suppression of appetite both result in improved glucose metabolism in mouse models of obesity and type 2 diabetes. A well-characterized example of this is the adipocytokine leptin. Leptin acts in the hypothalamus and hindbrain to suppress appetite and through stimulation of the autonomic nervous system increases oxidative metabolism in skeletal muscle (16-20). However, leptin can also improve hepatic insulin sensitivity independently of marked effects on food intake or body weight (17).

Infusion of fatty acids (FA) is associated with rapid reductions in insulin sensitivity in muscle within 4-6 h (21-23). The exact mechanism by which FA's reduce insulin-stimulated glucose uptake remains a matter of debate. Recent data indicate that FA's interfere with the IR signal transduction pathways that stimulate glucose uptake (21,22,24). One hypothesis is that an increase in the intracellular concentration of FA's and diacyl-glycerol leads to the activation of a serine kinase, protein-kinase C θ (PKCθ) (25). Phosphorylation of IRS1 on $Ser^{307}$ by PKCθ inhibits the phosphorylation of IRS-1 by the IR, leading to reduced activation of PI3K and a reduction in the stimulation of glucose uptake by insulin.

Abnormal Activity of Secreted Polypeptides as a Link Between Obesity and Insulin Resistance.

Determining mechanisms linking obesity with insulin resistance is important for developing new glucose lowering therapies. Recent research investigating insulin resistance has focused on adipocytes. Obesity is associated with aberrant regulation and function of a regulatory network of polypeptides secreted from adipocytes (adipocytokines). Adipocytokines such as leptin, adiponectin, and resistin regulate hepatic glucose production, glucose disposal in muscle, and the proliferation and storage of lipid in adipocytes (26). Leptin regulates energy homeostasis through effects on neurons located in the hypothalamus and hindbrain, regulating ingestive behavior, autonomic nervous activity, and neuroendocrine system that govern metabolism (thyroid, adrenals) (16). Leptin resistance or reduced serum adiponectin associated with obesity are factors that contribute to insulin resistance, through diminished insulin-sensitizing actions and by increasing risk for developing steatosis (intracellular fatty acid accumulation) (27,28). Non-adipose tissues also secrete peptides that affect energy metabolism and insulin sensitivity, such as musclin from muscle (29) and angiopoietin-related growth factor from liver (30). These factors may also be targets for the treatment of the metabolic syndrome.

Melanocortin Receptor Knockouts for Investigating the Link Between Obesity and Insulin Resistance:

Two melanocortin receptors expressed in areas of the central nervous system are involved in energy homeostasis. Targeted deletion of the neuronal melanocortin-4 receptor (MC4R) gene in mice (Mc4r−/− or Mc4rKO mice) causes obesity and hyperinsulinemia, and is also associated with increased hepatic lipogenic gene expression and hepatic steatosis. Mice deficient for another neuronal melanocortin receptor (Mc3r−/− or Mc3rKO mice) develop a similar degree of obesity to Mc4r−/− mice when fed a high fat diet, but do not exhibit the same level of insulin resistance, hyperlipidemia and increased hepatic steatosisWork Mc3rKO and Mc4rKO on the C57BL/6J (B6) strain both exhibit an exaggerated diet-induced obesity, however the deterioration of insulin sensitivity in Mc4rKO is more rapid and severe (31, 32). FIGS. 1A-1E illustrate some of the known differences in wild-type mice (C57BL/6J) and the two knockout mice in terms of body mass as a function of either a low fat diet or a high fat diet. (31,32) Severe insulin resistance in mice and humans is associated with hepatomegaly and steatosis, with increased hepatic lipogenesis (33). Mc4rKO develop hepatic insulin resistance and hepatomegaly in the obese state, and on a high fat diet (HFD) exhibit a marked deterioration of glucose homeostasis associated with severe glucose and insulin intolerance. FIGS. 2A-2E show the differences in hepatomegaly and steatosis in the two mouse strains, and also differences in expression of genes involved in lipid metabolism. (4,17,57) On the other hand, Mc3rKO matched to Mc4rKO for fat mass (FM) exhibit a very modest impairment of glucose homeostasis.

Sequences of cDNA Similar to Enho1.

A sequence and putative open reading frame of a cDNA encoding a putative protein homologous to ENHO1 have previously been published by several consortiums involved in large-scale sequencing of cDNAs. See R. L. Stausberg et al., "Generation and initial analysis of more than 15,000 full-length human and mouse cDNA sequences," Proc. Natl. Acad. Sci. U.S.A., vol. 99, pp. 16899-16903 (2002) (Genbank accession number: BC021944, cDNA with complete coding sequence); and H. F. Clark et al., "The secreted protein discovery initiative (SPDI), a large-scale effort to identify novel human secreted and transmembrane proteins: a bioinformatics assessment," Genome Res., vol. 13, pp. 2265-2270 (Genbank accession number: NM_198573, cDNA with complete coding sequence). A protein with similar homology for the first 37 amino acid residues of SEQ ID NO:2 has been identified. However, the nucleotide and amino acid sequence of this described protein may be incorrect, due to a single nucleotide error in the sequencing of the cDNA.

DISCLOSURE OF INVENTION

We have discovered a novel secreted peptide (Enho1) based on an investigation using two transgenic murine models of obesity. Using microarray gene expression analysis and validation by RealTime quantitative PCR, the expression of an mRNA (genbank accession number: AK009710) encoding a putative 76 amino acid, secreted protein was found to be reduced 10-fold in severely insulin resistant and glucose intolerant Mc4rKO and Leptin-deficient ($Lep^{ob}/Lep^{ob}$) mice. In contrast, in obese Mc3rKO mice, which are moderately glucose intolerant but exhibit a normal response to insulin, there was a modest 30-40% reduction in the expression of the Enho1 protein. In C57BL/6J mice, a negative correlation was found in the hepatic expression Enho1 mRNA with fasting glucose levels. The expression of Enho1 in the hypothalamus also declined with obesity and insulin resistance. We also confirmed that the mRNA encoded a secreted protein. Based on the negative effect of diet-induced obesity and insulin resistance on Enho1 mRNA expression in liver and brain, the gene encoding the protein was initially designated "Swirl" ("suppressed with insulin resistance"), but was later renamed "Enho1" ("energy homeostasis associated-1"). A recombinant adenovirus was used to increase the expression of ENHO1 in mouse models of obesity. Over-expression of ENHO1 by adenovirus injection significantly and reproducibly reduced fasting insulin, triglyceride and cholesterol levels. Additionally, the expression of a key gene involved in lipogenesis (fatty acid synthase) and FAS protein levels were reduced by ENHO1 adenoviral treatment in $Lep^{ob}/Lep^{ob}$ mice.

A transgenic FVB/NJ strain of mouse was created which over expresses the Enho1 open reading frame, using Enho1 DNA (SEQ ID NO:1) controlled by the human β-actin promoter which is expressed in all tissues. Female FVB/NJ mice over expressing Enho1 had a significant reduction in fat mass, and a higher metabolic rate determined by measuring oxygen consumption (VO2) using indirect calorimetry (Oxymax, Columbus Instruments, Columbus, Ohio). The increase in metabolic rate observed in the transgenic mice had been predicted, based on the results from experiments using recombinant adenovirus expressing Enho1. Mice infected with recombinant adenovirus expressing Enho1 lost more weight during an overnight fast, suggesting an impaired ability to reduce metabolic rate to compensate during fasting. FVB/NJ Enho1 transgenic mice exhibit the same exaggerated weight loss during a fast, associated with a higher metabolic rate. A component of Enho1's anti-diabetic actions may therefore involve stimulation of pathways involved in oxidative metabolism. That is, Enho1 may improve the metabolic profile of obese, insulin resistant individuals partially through normalizing the balance of kJ consumption with kJ expended through effects on physical activity, basal metabolic rate, or a combination of both.

Full-length Enho1 peptide, or peptide derivatives, homologues, analogues, or mimetics thereof, delivered by oral intake, injection, subcutaneous patch, or intranasal routes, could be used as therapeutic or diagnostic agents for hypercholesterolemia, hypertriglyceridemia, insulin resistance, obesity, diabetes, and/or disorders of energy imbalance.

Antibodies (AB1) and AB2 were raised against peptide fragments derived from the open reading frame predicted for BC021944, and shown in FIG. 5 as SEQ ID NO:8 and SEQ ID NO:9, respectively. These antibodies were used to verify the presence of Swirl-immunoreactivity in human serum and in rat brain, strongly supporting the conclusion that the open reading frame predicted for BC021944 encodes a small secreted peptide. Swirl-immunoreactivity was detected in human plasma. (data not shown) In rat brain, neurons with Swirl immunoreactivity have been identified in the arcuate nucleus of the hypothalamus. The significance of this observation is that neurons in the arcuate nucleus of the hypothalamus have been implicated in the regulation of energy expenditure, through effects on both facultative thermogenesis and physical activity, and on glucose homeostasis [Cone R D. Anatomy and regulation of the central melanocortin system. Nat Neurosci. 2005 May; 8(5):571-8; Coppari R, Ichinose M, Lee C E, Pullen A E, Kenny C D, McGovern R A, Tang V, Liu S M, Ludwig T, Chua S C Jr, Lowell B B, Elmquist J K. The hypothalamic arcuate nucleus: a key site for mediating leptin's effects on glucose homeostasis and locomotor activity. Cell Metab. 2005 January; 1(1):63-72.] The increased energy expenditure and physical activity of the FVB/NJ Swirl transgenic mice may therefore involve action in the central nervous system, and more specifically through actions based on regulating activity of neurons in the arcuate nucleus of the hypothalamus.

BRIEF DESCRIPTION OF THE DRAWINGS

FIG. 2A illustrates a comparison of liver histology, as shown in liver cross-sections stained with hemotoxylin and eosin, from female mice fed a high fat diet among three mice strains, wild-type (WT), Mc3r −/− deficient mice (Mc3rKO), and Mc4r −/− deficient mice (Mc4rKO).

FIG. 2B illustrates the differences in liver weight as a function of adiposity (percent body fat) in mice fed both low and high fat diets among three mice strains, wild-type (WT), Mc3r −/− deficient mice (Mc3rKO), and Mc4r −/− deficient mice (Mc4rKO).

FIG. 2C illustrates the differences in mean liver weight (n=5-6/group) of male and female mice fed a moderate high fat diet among three mice strains, wild-type (WT), Mc3r −/− deficient mice (Mc3rKO), and Mc4r −/− deficient mice (Mc4rKO). ("*" indicates $p<0.05$ versus WT and Mc3rK0 mice).

FIG. 2D illustrates the differences in expression of stearoyl-CoA desaturase 1 (SCD1) in liver of mice fed a high fat diet among three mice strains, wild-type (WT), Mc3r −/− deficient mice (Mc3rKO), and Mc4r −/− deficient mice (Mc4rKO). Data is expressed as arbitrary units (a.u.). ("*" indicates $p<0.05$ versus WT and Mc3rK0 mice).

FIG. 2E illustrates the differences in expression of apolipoprotein A4 (ApoA4) in liver of mice fed a high fat diet in three mice strains, wild-type (WT), Mc3r −/− deficient mice (Mc3rKO), and Mc4r −/− deficient mice (Mc4rKO). ("*" indicates $p<0.05$ versus WT and Mc3rK0 mice; "#" indicates $p<0.05$ versus WT mice, within gender).

FIG. 4 illustrates the nucleic acid sequence of the Enho1 gene (Mouse AK009710; SEQ ID NO:1), with the open reading frame encoding the Enho1 protein underlined, and its putative amino acid translation product Enho1 (SEQ ID NO:2).

FIG. 5 illustrates the alignment of the putative Enho1 protein sequences for mouse (SEQ ID NO:2), human (SEQ ID NO:14), rat (SEQ ID NO:12), dog (SEQ ID NO:15), pig (SEQ ID NO:16), cow (SEQ ID NO:17), sheep (SEQ ID NO:18), and chimpanzee (SEQ ID NO:13), showing the regions of the putative secreted polypeptide used to generate polyclonal antibodies (pAB1 ((SEQ ID NO:8) and pAB2 (SEQ ID NO:9)).

FIG. 6A illustrates the results of a Northern blot analysis using a radioactive-labeled portion of the AK009710 DNA sequence encoding Enho1 protein on human tissue samples (Lanes 1-8 represents RNA from heart, brain, placenta, lung, liver, skeletal muscle, kidney and pancreas, respectively).

FIG. 6B illustrates the relative intensity of Enho1 mRNA bands from a Northern blot analysis using the full-length mouse AK009710 DNA probe on mouse tissue samples.

FIG. 6C illustrates the results of a Western blot analysis for FLAG immunoreactivity in media (M) and cell lysates (Pel) from HEK293 human-kidney derived cells transfected with pCMV-Enho1:Flag, pCMV-GFP, or in media from HEK293 cells infected with adenoviral vector expressing Enho1:Flag fusion protein [no transfected DNA (lanes 1,2); transfected with a pCMV-Enho1:FLAG construct (lanes 3,4); transfected with pCMV-Enho1 (lanes 5,6); or transfected with pCMV-GFP (lanes 7,8); infected with Ad5Enho1:FLAG (lane 9); infected with Ad5Enho1 (lane 10); or infected with Ad5GFP (lane 11)]. To visualize Enho1 protein, a fusion protein was created with a C-terminal FLAG-epitiope tag.

FIG. 6D illustrates the results of a Western blot analysis for ENHO1 protein in various tissues (liver, muscle, and brain) from Mc4r−/− mice injected with Ad5-ENHO1:FLAG 4 days prior to the assay, along with controls, both positive (HEK293 cells infected with Ad5-ENHO1:FLAG) and negative (Liver from non injected Mc4r−/− mice).

FIG. 7A illustrates the results of a Western blot analysis using lysate from HEK293 cells infected with recombinant Ad5Enho1 (native protein) or Ad5Enho1:FLAG (C-terminal FLAG-tagged fusion protein) after incubation with a polyclonal antibody (pAB1) against the N-terminus of Enho1 (as shown in FIG. 5).

FIG. 7B illustrates the results of a Western blot analysis using lysate from HEK293 cells infected with recombinant Ad5Enho1 (native protein) or Ad5Enho1:FLAG (C-terminal FLAG-tagged fusion protein) after incubation with a polyclonal antibody (pAB2) against the C-terminus of Enho1 (as shown in FIG. 5).

FIG. 7C illustrates the treatment protocol used to administer Ad5Enho1 or Ad5-GFP into the tail vein of various strains of mice to test the effects of Enho1 treatment on mice metabolism (results presented in Table 1).

FIG. 8A illustrates the expression level of fatty acid synthase (Fasn) mRNA in liver from obese leptin-deficient ($Lep^{ob}/Lep^{ob}$) mice eight days after injection with either Ad5-ENHO1 or Ad5-GFP. Data expressed in arbitrary units (AU) (n=6-8/group; "*" p<0.05).

FIG. 8B illustrates the expression level of stearoyl-CoA desaturase (Scd1) protein in liver from obese leptin-deficient ($Lep^{ob}/Lep^{ob}$) mice eight days after injection with either Ad5-ENHO1 or Ad5-GFP. Data expressed in arbitrary units (AU) (n=6-8/group; "*" p<0.05).

FIG. 8C illustrates the expression level of acetyl CoA carboxylase (Acc) mRNA in liver from obese leptin-deficient ($Lep^{ob}/Lep^{ob}$) mice eight days after injection with either Ad5-ENHO1 or Ad5-GFP. Data expressed in arbitrary units (AU) (n=6-8/group; "*" p<0.05).

FIG. 8D illustrates the expression level of a gene involved in insulin resistance (a suppressor of cytokine signaling) in liver from obese leptin-deficient ($Lep^{ob}/Lep^{ob}$) mice eight days after injection with either Ad5-ENHO1 or Ad5-GFP. Data expressed in arbitrary units (AU) (n=6-8/group; "*" p<0.05).

FIG. 9A illustrates the construction of the transgene (BAP-Enho1) used to generate transgenic mouse strains that over express Enho1.

FIG. 9B illustrates the amount of Enho1 expression in livers from transgenic mice pups (produced using the transgene of FIG. 9A) from FVB/NJ founders at 5 weeks.

FIG. 9C illustrates the level of fasting triglycerides (TG) from serum of transgenic mice pups (produced using the transgene of FIG. 9A) from FVB/NJ founders at 9 weeks.

FIG. 9D illustrates the body composition as measured by percent body fat (% body fat; left graph) and fat mass (showing both free fat mass (FFM) and fat mass (FM); right graph) in transgenic mice pups (produced using the transgene of FIG. 9A) from FVB/NJ founders at 5 and 9 weeks as compared with control.

FIG. 9E illustrates change in fat mass (showing both free fat mass (FFM) and fat mass (FM)) of transgenic mice pups (produced using the transgene of FIG. 9A) from FVB/NJ founders after 7 days on a 60% high fat diet.

MODES FOR CARRYING OUT THE INVENTION

The present invention discloses a novel secreted protein (Enho1) and identifies some of its functions. The sequence of this protein was found to be highly conserved across several mammalian species, and the sequences are shown in SEQ ID NOS:2 and 12-18. In addition the nucleic acids that encode this protein was used to make mice that over expressed the Enho1 protein, either by infection with a recombinant adenovirus expressing Enho1 or by making a transgenic strain using Enho1 DNA controlled by an actin promoter.

In one embodiment, the Enho1 protein, fragment, derivative or analogs are used therapeutically to prevent a pathophysiology associated with increased body mass, e.g., obesity, hyperglycemia, hyperinsulinemia, insulin resistance, hyperlipidemia, and non-insulin dependent (type 2) diabetes mellitus.

In another embodiment, the purified Enho1 protein, fragment, derivative or analog is isolated from various mammals, or made synthetically, or made using cell cultures that express the protein.

In another embodiment, antibodies are made to the Enho1 protein, its fragments, derivatives or analogs. These antibodies can be used in a kit to identify the Enho1 protein from various samples, including body fluids.

In another embodiment, transgenic animals are made that over express the Enho1 protein by linking the Enho1 sequence to an active promoter, e.g., an actin promoter. In another embodiment, a transformation vector comprising at least the open reading frame of SEQ ID NO:1 (the portion underlined in FIG. 4) are made.

Example 1

Discovery of Enho1 Protein and Its Function

Microarrays analyzing hepatic gene expression in lean and obese Mc3rKO were performed using arrays printed from libraries of 16,463-18,400 70-mer oligonucleotides (Mouse Array-Ready Oligo Set Version 2.0, Qiagen Operon, Alameda, Calif.) (34-36). The microarray data indicated increased expression of genes involved in lipid metabolism (apoliproteins) and oxidative stress secondary to obesity. Interestingly, the expression of only three genes was reduced in liver of Mc3rKO irrespective of age, gender, and adiposity. Two of the genes encoded proteins with known function: neuraminidase 3 (neu3), encoding an enzyme that cleaves sialic acid from glycoproteins and glycolipids, and solute carrier family 21 (slc21a1) which encodes an organic anion transporter. The third gene (AK009710) was novel and had no assigned function in the databases.

Figure 1A:
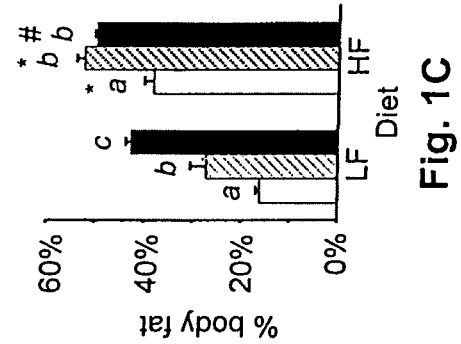
FIG. 1A illustrates the differences in body mass in 6-month-old, female mice after 12 weeks feeding either a low-fat diet (LF) or a high-fat diet (HF) among three different strains, wild-type (WT), Mc3r −/− deficient mice (Mc3rKO), and Mc4r −/− deficient mice (Mc4rKO). (Significant effect of diet is indicated by "*" ($p<0.001$) or "#" ($p<0.05$); significant effects within diet indicated by letters, with groups significantly different ($p<0.05$) given different letters; significance based on 2-way AVOVA)
Figure 1B:
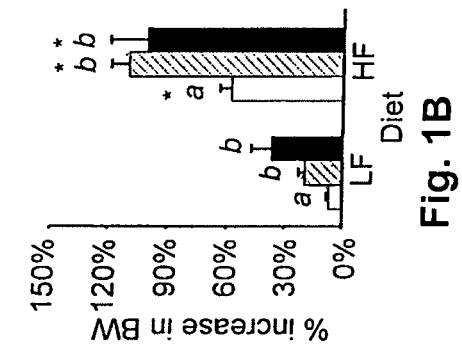
FIG. 1B illustrates the differences in body weight gain as a percent of starting weight in 6-month-old, female mice after 12 weeks feeding either a low-fat diet (LF) or a high-fat diet (HF) among three different strains, wild-type (WT), Mc3r −/− deficient mice (Mc3rKO), and Mc4r −/− deficient mice (Mc4rKO). (Significant effect of diet is indicated by "*" ($p<0.001$) or "#" ($p<0.05$); significant effects within diet indicated by letters, with groups significantly different ($p<0.05$) given different letters; significance based on 2-way AVOVA)
Figure 1C:
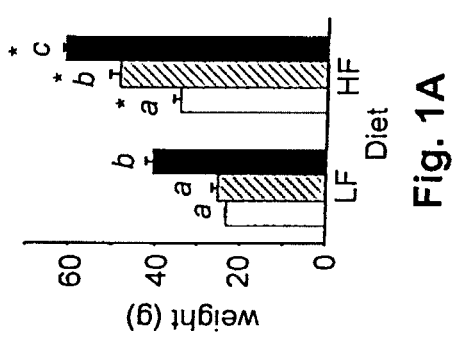
FIG. 1C illustrates the differences in percent body fat in 6-month-old, female mice after 12 weeks feeding either a low-fat diet (LF) or a high-fat diet (HF) among three different strains, wild-type (WT), Mc3r −/− deficient mice (Mc3rKO), and Mc4r −/− deficient mice (Mc4rKO). (Significant effect of diet is indicated by "*" ($p<0.001$) or "#" ($p<0.05$); significant effects within diet indicated by letters, with groups significantly different ($p<0.05$) given different letters; significance based on 2-way AVOVA)
Figure 1D:
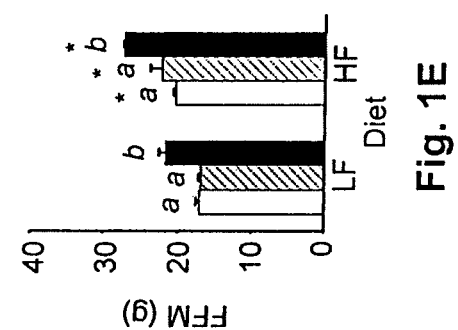
FIG. 1D illustrates the differences in fat mass in 6-month-old, female mice after 12 weeks feeding either a low-fat diet (LF) or a high-fat diet (HF) among three different strains, wild-type (WT), Mc3r −/− deficient mice (Mc3rKO), and Mc4r −/− deficient mice (Mc4rKO). (Significant effect of diet is indicated by "*" ($p<0.001$) or "#" ($p<0.05$); significant effects within diet indicated by letters, with groups significantly different ($p<0.05$) given different letters; significance based on 2-way AVOVA)
Figure 1E:
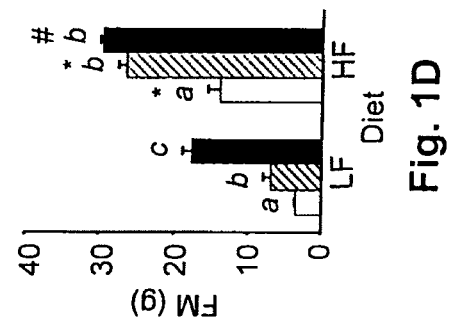
FIG. 1E illustrates the differences in fat-free mass in 6-month-old, female mice after 12 weeks feeding either a low-fat diet (LF) or a high-fat diet (HF) among three different strains, wild-type (WT), Mc3r −/− deficient mice (Mc3rKO), and Mc4r −/− deficient mice (Mc4rKO). (Significant effect of diet is indicated by "*" ($p<0.001$) or "#" ($p<0.05$); significant effects within diet indicated by letters, with groups significantly different ($p<0.05$) given different letters; significance based on 2-way AVOVA)
Figure 3A:
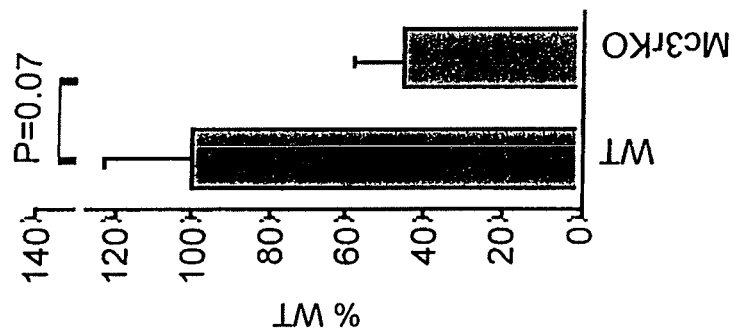
FIG. 3A illustrates the amount of hepatic AK009710 mRNA expression (given as a percent of WT expression) in wild-type (WT) mice and in obese Mc3r −/− deficient mice (Mc3rKO).
Figure 3B:
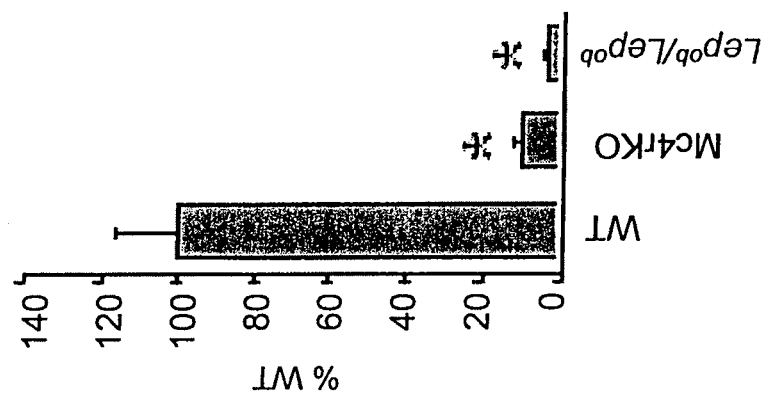
FIG. 3B illustrates the amount of hepatic AK009710 mRNA expression (given as a percent of WT expression) in wild-type mice (WT), Mc4r −/− deficient mice (Mc4rKO), and leptin-deficient $Lep^{ob}/Lep^{ob}$ mice (two models of obesity).
Figure 3C:
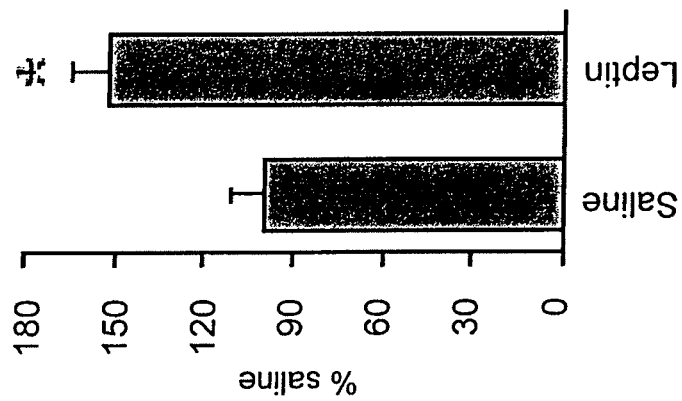
FIG. 3C illustrates the amount of hepatic AK009710 mRNA expression (given as a percent of expression with saline) in leptin-deficient $Lep^{ob}/Lep^{ob}$ mice injected 4 times over 2 days with either saline or leptin (0.5 mg/g).

Quantitative RealTime PCR confirmed the microarray data showing a tendency for a modest reduction in the expression of AK009710 in liver of Mc3rKO (FIG. 3A). Intriguingly, a more dramatic reduction in the expression of AK009710 was observed in liver of severely insulin resistant Mc4rKO and leptin-deficient (Lep$^{ob}$/Lep$^{ob}$) mice (FIG. 3B). In addition, short term treatment with leptin (4 injections of 0.5 mg/g leptin over 2 days) significantly increased Enho1 in the liver of Lep$^{ob}$/Lep$^{ob}$ mice. (FIG. 3C). Expression of AK009710 in 6 wk old lean Mc4rKO is normal (data not shown), indicating that the decline in liver expression of Mc4rKO is secondary to the age-related onset of obesity, insulin resistance and hepatic steatosis (32). Moreover, AK009710 expression correlated negatively with fasting glucose in diet-induced obese B6 mice (n=13, $R^2$=0.67, P<0.001) (data not shown).

Overall, these results indicate the identification of a small secreted protein whose expression in liver declines with insulin sensitivity and hepatic steatosis. Based on the observation that the decline in AK009710 expression in liver correlates with the severity of hepatic steatosis and insulin resistance, and that this decline is reversed by an insulin sensitizor, the name "suppressed with insulin resistance 1" (swir1) was chosen, but later renamed "energy homeostasis associated-1" (Enho1).

Oligonucleotide primers targeted to AK009710 mRNA were utilized to measure AK009710 gene expression in liver cDNA from various mouse models of obesity and insulin resistance. Sequences of primers were: sense 5-cctgagggtgct-gtctgtcatg-3' (SEQ ID NO:3), antisense 5'-cagtagcagcaa-gaagcctacg-3' (SEQ ID NO:4), probe 5'-6FAM-ctctcatcgc-catcgtctgca-BHQ-3' (SEQ ID NO:5). In agreement with the initial microarray result, AK009710 mRNA was down regulated in the liver of Mc3r-/- mice compared to WT mice (by 55%, p<0.05; FIG. 3A). Next was examined the AK009710 liver mRNA expression in two other models of obesity: Mc4r-/- mice and leptin-deficient Lep$^{ob}$/Lep$^{ob}$ mice. AK009710 mRNA was expressed at approximately 10-fold lower levels in both of these models compared to wild-type mice (WT) (FIG. 3B). When all animals were grouped together negative relationships between AK009710 mRNA expression and glucose and insulin values were observed (Data not shown). AK009710 gene expression was not altered in the liver of young and aged WT mice fed ad libitum, fasted for 16 h, or fasted for 24 h and re-fed for 4 h. (data not shown) AK009710 is not thought to be altered by nutritional status.

In order to determine whether AK009710 mRNA might be regulated secondary to the development of insulin resistance, AK009710 mRNA was measured in the liver of young, normoinsulinemic and older hyperinsulinemic Mc4r-/- mice. AK009710 mRNA was observed to be similar to the wild-type mice in young Mc4r-/- mice (average age ~7 weeks), whereas it was significantly reduced in older (~16 weeks) Mc4r-/- mice. (data not shown). Furthermore, AK009710 mRNA was also measured in a small number (n=4) of human-derived hepatocytes from diabetic and non-diabetic subjects. Although the expression tended to be lower in the diabetic samples, the difference was not statistically significant (data not shown).

Thus, while obesity of Mc3r-/- and Mc4r-/- mice is similar, insulin resistance and elevated serum lipids (triglyceride, cholesterol) are known to be far more severe for Mc4r-/- mice. The reduction in AK009710 gene expression in the liver correlated with the known severity of insulin resistance and hyperlipidemia in Mc4r-/- mice.

Example 2

Sequence and Bioinformatics Analysis

AK009710 is a mouse tongue cDNA clone 1247 by in length and belongs to the Unigene cluster Mm.34074, 2310040A07Rik: RIKEN cDNA 2310040A07 gene. It hypothetically could encode a 534 amino acid protein immediately from the 5' end of the sequence. Given that this putative protein did not start with a methionine residue, it was listed as a truncated product. BLAST analysis of AK009710 for homologous EST or cDNA sequences on the NCBI database revealed a significant match with NM198573, a human transcript discovered by a large-scale Secreted Protein Discovery Initiative encoding a hypothetical protein of 87 aa (UNQ470/GAAI470) (37). The match with human sequence—NM_198573 was 85% identity across 392 nucleotides, p=5e$^{-83}$. The human sequence encoded an 87 amino acid protein in one exon. Translation of AK009710 in six frames revealed an open reading frame encoding a 76 amino acid protein (SEQ ID NO:2). An alignment between this putative mouse protein and the human protein encoded by NM_198573 (GAAI470, or UNQ470) revealed strong homology over the first 37 residues. UNQ470/GAAI470 maps to chromosome 9p13.2. and is adjacent to the ciliary neurotrophic factor receptor (CNTFR) gene.

The sequence of AK009710 was verified using cDNA isolated from mouse liver. Moreover, an 868 by cDNA cloned from mouse liver by the National Institutes of Health Mammalian Gene Collection (MGC) Program, with the accession number BC021944, recently posted on the NCBI database agrees with our sequencing data. (FIG. 4, SEQ ID NO:1) BLAST analysis revealed that the predicted 76 aa sequence for mouse (SEQ ID NO:2) is highly conserved in several mammalian species (FIG. 5; SEQ ID NO:12 (rat), SEQ ID NO:13 (chimpanzee); SEQ ID NO:14 (human); SEQ ID NO:15 (dog); SEQ ID NO:16 (pig); SEQ ID NO:17 (cow); SEQ ID NO:18 (sheep)). In FIG. 5, pAB1 (SEQ ID NO: 8) and pAB2 (SEQ ID NO:9) refer to the regions of the putative secreted polypeptide used to generate polyclonal antibodies. The predicted signal sequence is underlined. In addition peptides were synthesized corresponding to amino acids 34 through 76 (Enho1$^{34-76}$; SEQ ID NO:10), and to amino acids 39 through 76 (Enho1$^{39-76}$; SEQ ID NO:11) of SEQ ID NO:2, the mouse protein.

Figure 4:
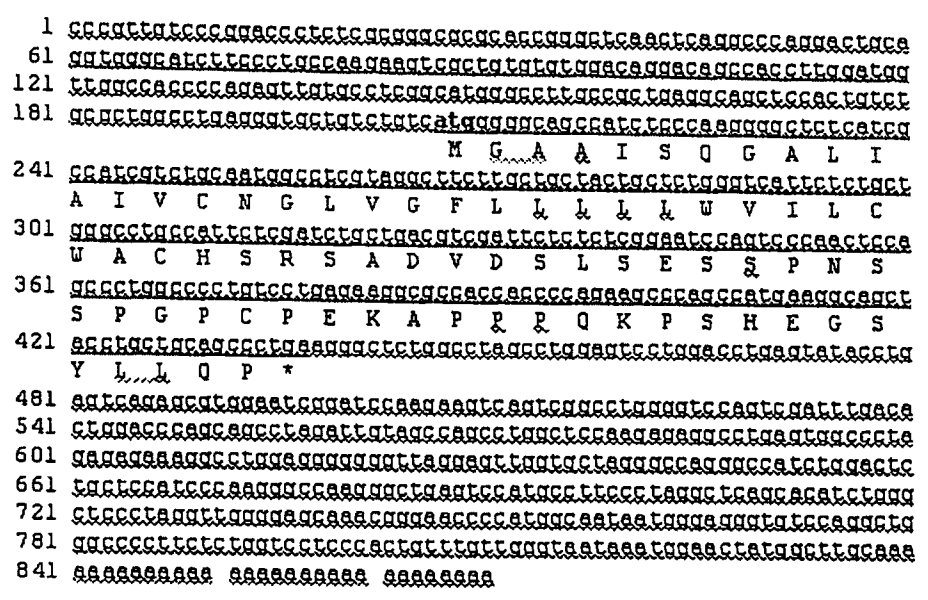

Further analysis of the putative mouse sequence from AK009710 and the human GAAI470 sequence revealed a single nucleotide gap in the human sequence on GenBank. Therefore a mouse AK009710 PCR product was cloned and sequenced in both directions to confirm which sequence, either the mouse or the human, was correct. The sequence-verified AK009710 mouse clone revealed a 76 amino acid translation product (SEQ ID NO:2) (FIG. 4). A publicly available Origene clone of human GAAI470 was analyzed and shown not to contain the nucleotide gap, indicating a sequencing error in the NM_198573 sequence on GenBank. Alignment of AK009710 sequence from different species, including human, revealed a 100% homology between rat, human, mouse and chimp sequences at the protein level (FIG. 5).

Bioinformatics analysis revealed that this protein is highly likely to be a secreted peptide (87% probability, SignalP 3.0) with the most likely cleavage site between positions 33 and 34. The human sequence contains 1 possible serine site, and 1 possible threonine phosphorylation sites, all 3' to the predicted cleavage point, as well as 6 possible glycosylation sites, also all 3' to the cleavage site.

Example 3

Tissue Distribution of Enho1

In order to examine the tissue distribution of AK009710 mRNA a Northern blot was performed using the 210 nt sequence containing the 76 amino acid protein ENHO1 and a human Multiple Tissue Northern blot (BD Biosciences, Palo Alto, Calif.). As can be seen in FIG. 6A, a single band of ~1.35 kb was detected in humans in brain and liver samples only, with highest levels detected in the liver. However, as seen in FIG. 6B, Enho1 was found in mice in the liver, brain, and muscle.

Example 4

Confirmation that Enho1 is a Secreted Polypeptide

Bioinformatics analysis predicted the presence of a putative signal sequence suggesting that AK009710 is a secreted peptide. To test this, the coding sequence of the 76 amino acid protein was amplified from mouse liver cDNA by PCR using primers with NotI (5'-ggggcggccgcaccatgggggcagc-catctcccaa-3' (SEQ ID NO:6)) and XhoI (5'-gggctcgagggcca-gagcccttcagggctgcag-3' (SEQ ID NO:7)) restriction enzyme sites attached. The product was ligated into a pCMV-Tag1 vector with a FLAG epitope at the C-terminal end (pCMV-Enho1:FLAG), then transiently transfected into HEK human kidney-derived cells. This product was also used to create two adenoviral constructs—one with Enho1 attached to a FLAG epitope (Ad-Enho1:FLAG), and another without the FLAG epitope (Ad-Enho1).

HEK293 cells were transfected with pCMV-Enho1, or pCMV-Enho1:FLAG. Media was collected after 16 h, immunoprecipitated, and then run on a 20% polyacrylamide gel to be visualized by an anti-FLAG antibody. These experiments were repeated using recombinant adenovirus (Ad5) expressing native or FLAG-tagged Enho1.

When HEK293 cells were untransfected (lanes 1,2), or transfected with empty vector (lanes 5,6), or vector containing GFP (lanes 7,8) no FLAG-immunoreactive bands were visualized (FIG. 6C). However, when the pCMV-Enho1:FLAG construct was transfected into HEK293 cells (lanes 3,4), FLAG-positive immunoreactivity was detected in both the media and the cell pellet, indicating that at least some of the transfected Enho1 product was being actively secreted by the cells into the media. Similar results were observed in the media of HEK293 cells infected with Ad-Enho1:FLAG (FIG. 8, lane 9). Lanes 10 and 11 show no FLAG immunoreactivity in media of cells infected with adenovirus containing Enho1 without the FLAG epitope, or with GFP, respectively. Thus the presence of FLAG immunoreactivity in cultured media of HEK-293 cells transfected with an expression vetor expressing an epitope-tagged fusion protein (pCMV-Enho1FLAG) confirmed that an undefined portion of the 76 aa protein is secreted.

Most adenovirus injected in the tail vein infects liver (38). To test whether tail vein injection of adenovirus leads to increased expression of ENHO1 mRNA in the liver, as well as other tissues, three Mc4r−/− mice were injected with Ad5-ENHO1:FLAG adenovirus and the tissues collected after four days. Analysis by Western blot revealed the presence of FLAG immunoreactivity in the liver, muscle and brain tissue indicating the presence of ENHO1 in these tissues. (FIG. 6D) The distribution of Enho1FLAG immunoreactivity in tissues of mice infected with Ad5-Enho1FLAG is consistent with a polypeptide secreted into the circulatory system from liver. Both of these tests indicated that Enho 1 is a secreted protein.

Example 5

Treatment of Obese Insulin Resistant Mice with Ad5-Enho1:Mc4rKO

Recombinant adenoviral vector-mediated expression has been used to investigate regulation of liver metabolism and insulin sensitivity (39-41). Three recombinant adenovirus vectors were constructed expressing the 76 aa protein (Ad5-Enho1), a C-terminal FLAG-tagged fusion protein (Ad5-Enho1:FLAG), or green fluorescent protein for the negative control (Ad5-GFP). Expression of protein following tail vein injection was confirmed using anti-FLAG antibody (FIG. 6D and data not shown). Synthesis of Enho1 was confirmed in HEK293 cells transfected with Ad5-Enho1 using polyclonal antibodies (pAB1 & pAB2 in FIG. 5) against N- and C-terminal regions of the putative secreted protein (Sigma Genosys, The Woodlands, Tex.) (FIG. 7A, B).

To investigate whether ENHO1 is involved in glucose metabolism, Ad5-ENHO1 or Ad5-GFP ($5 \times 10^8$ pfu) was injected into the tail vein of 20-week-old male and female Mc4r−/− (n=3 of each sex per group). Both groups of animals were matched for body weight, glucose levels and glucose tolerance before Ad5-ENHO1 or Ad5-GFP injections. An intraperitoneal glucose tolerance test (IPGTT) was performed one week prior to injection of Ad5-ENHO1 or Ad5-GFP, and all mice were observed to be glucose intolerant. IPGTT were performed on mice after an overnight fast, with a single intraperitoneal injection of 1 g/kg glucose, and blood glucose measured with a blood glucose meter and test strips (Glucometer Elite, Bayer Corp., Elkhart, Ind.) from the tail blood of the animals at several intervals, as described by W. Fan et al., "The Central Melanocortin System Can Directly Regulate Serum Insulin Levels," Endocrinology, vol. 141, pp. 9 3072-3079 (2000).

Mice were injected with $5 \times 10^8$ pfu of Ad5-ENHO1 or Ad5-GFP in 100 µl of diluent (DMEM) into the tail vein. Animals were observed and weighed daily throughout the 4-day experiment. On day 4 animals were given another IPGTT (0.4 mg glucose/g body weight).

Four days after injection of Ad5-ENHO1, the mice demonstrated improved glucose tolerance as measured using IPGTT (data not shown). There was no change in body weight, blood glucose or cholesterol levels throughout the experiment. There was a trend for a decrease in insulin and serum triglyceride levels (Table 1).

TABLE 1

Characteristics of Mc4r −/− mice 4 days post adenoviral infusion.

| Group | Body Weight (g) | Glucose (mg/dL) | Insulin (ng/mL) | Cholesterol (mg/dL) | Triglycerides (ng/mL) |
|---|---|---|---|---|---|
| Ad5-ENHO1 | 50.4 ± 1.8 | 184 ± 10 | 5.9 ± 1.5 | 91 ± 7 | 26 ± 4 |
| Ad5-GFP | 49.5 ± 2.2 | 169 ± 16 | 10.4 ± 2.0 | 82 ± 6 | 38 ± 6 |

Example 6

Treatment of Obese Insulin Resistant Mice with Ad5-Enho1:B6 Ay/a

A second adenoviral experiment was performed whereby Ad5-ENHO1 or Ad5-GFP was injected into the tail vein of male C57BL6 Ay/a mice (n=9 per group) that had been maintained on a very high fat diet for ~3 months. Mice were given 1 week to recover from the injections, and then an IPGTT was performed. Then the mice were given another week to recover, and an insulin tolerance test (ITT) was performed.

No differences in body weight (40.3±1.3 g for the Ad5-ENHO1 mice; 41.4±1.2 g for the Ad5-GFP mice), fasting insulin (0.97±0.2 ng/mL for the Ad5-ENHO1 mice; 1.13±0.2 ng/mL for the Ad5-GFP mice), or fasting glucose levels (126±7 mg/dL for the Ad5-ENHO1 mice; 139±8 mg/dL for the Ad5-GFP mice) were observed at 20 days after injection. IPGTT 7 days after injection revealed a very modest improvement in glucose tolerance in the Ad5-ENHO1 group at the 30-minute (p=0.06) and 45-minute (p=0.15) time points. Changes in blood glucose levels 14 days after injection were significantly different between groups, being significantly reduced in the Ad5-ENHO1 group (data not shown). An ITT 14 days post-infection revealed no significant difference in insulin sensitivity at any time point; however Ki (calculated as glucose at 30 minutes post insulin injection subtracted from baseline glucose, divided by 30) was significantly different.

The lower fasting blood glucose levels observed in these mice 14 days after infection was not apparent at 21 days after infection. In agreement with the first adenoviral experiment in Mc4r−/− mice, there was a trend for a decrease in serum triglycerides in the Ad5-ENHO1 group (Table 2).

Ad5-GFPAd5-GFP treatment. Statistically significant reductions in circulating triglycerides (by 28%, p=0.04) and cholesterol (by 20%, p=0.02) were observed in the Ad5-ENHO1 group compared to Ad5-GFP controls (Table 1). Liver weight of Ad5-ENHO1 mice tended to be lower than liver weight of Ad5-GFP controls (Table 2). Body weight, and serum glucose and insulin levels were not significantly different between Ad5-ENHO1 and Ad5-GFP controls (Table 2).

TABLE 3

Characteristics of KK-A$^y$ mice treated with Ad5-ENHO1 or Ad5-GFP for 8 days.

| Treatment | Body Weight (g) | Liver weight (g) | Liver as % of body weight | Glucose (mg/dL) | Insulin (ng/mL) |
|---|---|---|---|---|---|
| Ad5-ENHO1 | 41.9 ± 0.9 | 1.8 ± 0.1 | 4.3 ± 0.1 | 239 ± 19 | 4.3 ± 0.7 |
| Ad5-GFP | 44.1 ± 1.5 | 2.1 ± 0.2 | 4.6 ± 0.2 | 246 ± 41 | 5.1 ± 0.9 |

ENHO1 mRNA was elevated approximately 4-fold in the liver of KK-A$^y$ Ad5-ENHO1-treated mice compared to Ad5-GFP-treated mice (data not shown).

Example 8

Treatment of Obese Insulin Resistant Mice with Ad5-Enho1:Lep$^{ob}$/Lep$^{ob}$ Mice To confirm the lipid-lowering effect of adenoviral-mediated ENHO1 overexpression, another experiment was performed in which Ad5-ENHO1 or Ad5-GFP was injected into the tail vein of Lep$^{ob}$/Lep$^{ob}$ (OBOB) mice (n=7-8 male per group), another mouse model of hyperlipidemia, steatosis

TABLE 2

Infection with Ad5-Enho1 is associated with evidence of improved metabolic profile in mouse models of obesity and insulin resistance.

| Strain | Treatment | BW pre-injection | BW post-injection | Liver wgt (g) | Liver wgt as a % BW | Liver lipid content (mg/g) | Total liver lipid (mg) | Serum TG (mg/dL) | Serum TC (mg/dL) | HOMA-IR |
|---|---|---|---|---|---|---|---|---|---|---|
| OBOB | GFP | 64.0 ± 1.9 | 64.8 ± 2.0 | 4.7 ± 0.2 | 7.4 ± 0.3 | 142 ± 8 | 654 ± 25 | 63 ± 6 | 173 ± 6 | 308 ± 114 |
|  | Enho1 | 65.0 ± 2.2 | 64.6 ± 2.0 | 4.3 ± 0.2 | 6.7 ± 0.3 | 128 ± 7 | 552 ± 50 | 38 ± 4* | 146 ± 8* | 157 ± 18 |
| KKAy | GFP | 48.0 ± 1.9 | 46.7 ± 1.7 | 2.1 ± 0.2 | 4.7 ± 0.3 | 57 ± 10 | 117 ± 24 | 435 ± 53 | 214 ± 13 | 98 ± 19 |
|  | Enho1 | 46.6 ± 1.2 | 45.3 ± 0.8 | 1.8 ± 0.1 | 4.3 ± 0.1 | 33 ± 2* | 58 ± 5* | 315 ± 16* | 172 ± 9 | 62 ± 11 |
| Ay/a | GFP | 45.2 ± 2.5 | 44.6 ± 2.1 | 2.2 ± 0.2 | 5.1 ± 0.2 | 119 ± 11 | 282 ± 39 | 71 ± 18 | 79 ± 3 | 40 ± 6 |
|  | Enho1 | 44.8 ± 1.4 | 44.5 ± 1.1 | 1.8 ± 0.2 | 4.2 ± 0.3* | 81 ± 20 | 145 ± 41* | 53 ± 4 | 72 ± 2 | 28 ± 4 |

*P < 0.05 compared to Ad5-GFP treated controls (within strain), n = 5-8/group.

Example 7

Treatment of Obese Insulin Resistant Mice with Ad5-Enho1:Agouti (KK-A$^y$) Mice (Genetically Obese and Hyperlipidemic Mice)

To more specifically address the effect of adenoviral infusion on measures of blood lipids, the adenoviral constructs were further purified to remove any contaminating viral particles and cellular debris. Another adenoviral experiment was then conducted whereby Ad5-ENHO1 or Ad5-GFPAd5-GFP was injected into the tail vein of genetically obese and hyperlipidemic KK-A$^y$ mice (n=6 female per group). Mice were given an IPGTT 5 days post virus injection, and then sacrificed 2 days later after an overnight fast.

IPGTT revealed that glucose tolerance was not significantly improved by Ad5-ENHO1 treatment compared to and insulin resistance. The injected mice were not given an IPGTT, but were monitored for body weight changes, and then sacrificed 7 days post injection after an overnight fast.

Ad5-GFP-treated mice gained approximately 1 g of body weight over the 7-day period. However, Ad5-ENHO1 treatment blocked weight gain in these obese Lep$^{ob}$/Lep$^{ob}$ mice (data not shown). Mean body weight was not statistically different between groups, and food intake was not measured. Similar phenotypic changes to that observed in KK-A$^y$ mice (See Example 7 above) were also observed. Serum triglycerides were reduced by 40% in the Ad5-ENHO1 group (Ad5-GFP 63±6 mg/dL (Ad5-GFP); 38±4 mg/dL (Ad5-ENHO1), p=0.006; Table 2). A 15% reduction in serum cholesterol levels was also observed (173±6 mg/dL (Ad5-GFP); 146±8 mg/dL (Ad5-ENHO1), p=0.02; Table 2). A trend for a reduction in liver weight was observed that was not significant when expressed as a percentage of body weight (p=0.12).

Trends for reduced fasting blood glucose and insulin levels in the Ad5-ENHO1 group did not reach statistical significance.

Purification of the adenoviral constructs and use of larger sample populations in the experiments using KK-A$^y$ mice and Lep$^{ob}$/Lep$^{ob}$ mice demonstrated that overexpression of ENHO1 for 7-8 days lead to reduced circulating triglyceride and cholesterol levels compared to control mice. (Table 2) Trends for these effects were observed in previous experiments using unpurified adenovirus with observations at later time points. ENHO1 gene expression in the liver was elevated in Ad5-ENHO1-treated group in these experiments, whereas no increase was detectable in previous experiments at later time points. Without wishing to be bound by this theory, it is believed that increased gene expression of ENHO1 leads to increased circulating levels of the ENHO1 protein.

Example 9

Summary of Results of Treatment of Obese Insulin Resistant Mice with Ad5-Enho1

In summary, 5×10$^9$ pfu of Ad5-Enho1 or Ad5-GFP was administered into the tail vein of KKAy, B6 Ay/a, or OBOB mice purchased from the Jackson Laboratory (Bar Harbor, Me.). The treatment protocol, shown in FIG. 7C, was based on the pilot experiments demonstrating peak expression of Ad5-Enho1:FLAG during this period (data not shown). Animal and food weight were recorded daily. Ad5-Enho1 infection was well tolerated in mouse strains used for these experiments. There were no marked differences in the body weight (Table 2) of mice infected with Ad5-Enho1 compared to controls infected with Ad5-GFP over the treatment period. A 4-5 fold increase in Enho1 mRNA was observed in mice infected with Ad5-Enho1, compared to Ad5-GFP treated controls (data not shown).

Liver weight and lipid content were consistently reduced in mice infected with Ad5-Enho1. In KKAy and OBOB mice, significant reductions (≈40%) in fasting triglyceride and total cholesterol were observed. A smaller decline was observed in Ay/a mice. Meta-analysis of data from several experiments using obese OBOB, KKAy and Ay/a mice mice indicated a 40% reduction of HOMA-IR [(fasting insulin×glucose)/22.5] in OBOB, KKAy and Ay/a mice (Table 4). In Ay/a mice, fasting insulin levels were significantly reduced with Ad5-Enho1 (2.6±0.4 vs. 3.9±0.3 ng/ml, P<0.05), with no difference in blood glucose (175±12 vs. 162±11 mg/dL).

TABLE 4

Meta-analysis of HOMA-IR, calculated by mutiplying fasting insulin and glucose, from OBOB, KKAy and Ay/a mice infected with Ad5-GFP or Ad5-Enho1.
Data are expressed as % ± SEM of control group.

| Ad5-GFP | Ad5-Enho1 | Student's t-test |
|---|---|---|
| 100 ± 12% | 62 ± 4% | P < 0.005 |

Example 10

Overexpression of ENHO1 Effects on Genes Involved in Lipid Biosynthesis

Reversal of hepatic steatosis by adipocytokines is at least partially attributable to the suppression of hepatic lipogenesis and stimulation of fatty acid oxidation (42,43). To investigate the mechanism by which Enho1 reduced hepatic lipid content, the expression of genes involved in lipogenesis was measured by quantitative RT-PCR (FIGS. 8A-8D). There was a coordinate 40-50% reduction in the expression of several genes involved in lipogenesis in the liver of OBOB and KKAy mice infected with Ad5-Enho1. Enho1 may therefore reduce hepatic lipid content, at least in part, by inhibiting hepatic lipogenesis.

A significant decrease in fatty acid synthase (Fasn) mRNA in the Ad5-ENHO1-treated group was observed compared to the Ad5-GFP controls (FIG. 8A, p=0.02), as well as a decrease in protein levels (data not shown). Fasn mRNA and protein levels were measured using quantitative RealTime PCR and western blot, as described in D. C. Albarado et al., "Impaired Coordination of Nutrient Intake and Substrate Oxidation in Melanocortin-4 Receptor Knockout Mice," Endocrinology, vol. 145, pp. 243-252 (2004). Gene expression of the fatty acid translocase CD36 was also significantly elevated in the Ad5-ENHO1 group (p=0.02, not shown). FIG. 8A illustrates the expression level of fatty acid synthase (Fasn) mRNA in liver from obese leptin-deficient (Lep$^{ob}$/Lep$^{ob}$) mice eight days after injection with either Ad5-ENHO1 or Ad5-GFP. Data expressed in arbitrary units (AU) (n=6-8/group; "*" p<0.05). Enho1 overexpression caused a decrease in Fasn. FIG. 8B illustrates the expression level of stearoyl-CoA desaturase (Scd1) protein in liver from obese leptin-deficient (Lep$^{ob}$/Lep$^{ob}$) mice eight days after injection with either Ad5-ENHO1 or Ad5-GFP. Data expressed in arbitrary units (AU) (n=6-8/group; "*" p<0.05). Again, Enho1 overexpression caused a decrease in Scd1. FIG. 8C illustrates the expression level of acetyl CoA carboxylase (Acc) mRNA in liver from obese leptin-deficient (Lep$^{ob}$/Lep$^{ob}$) mice eight days after injection with either Ad5-ENHO1 or Ad5-GFP. Data expressed in arbitrary units (AU) (n=6-8/group; "*" p<0.05). Again, the mice with Enho1 showed lower levels of liver Acc. FIG. 8D illustrates the expression level of a gene involved in insulin resistance (suppressor of cytokine signaling 3 or Socs3) in liver from obese leptin-deficient (Lep$^{ob}$/Lep$^{ob}$) mice eight days after injection with either Ad5-ENHO1 or Ad5-GFP. Data expressed in arbitrary units (AU) (n=6-8/group; "*" p<0.05). The presence of Enho1 again decreased the gene express of Socs3.

Example 11

Transgenic Over Expression of Enho1 (BAP-Enho1)

Figure 10:
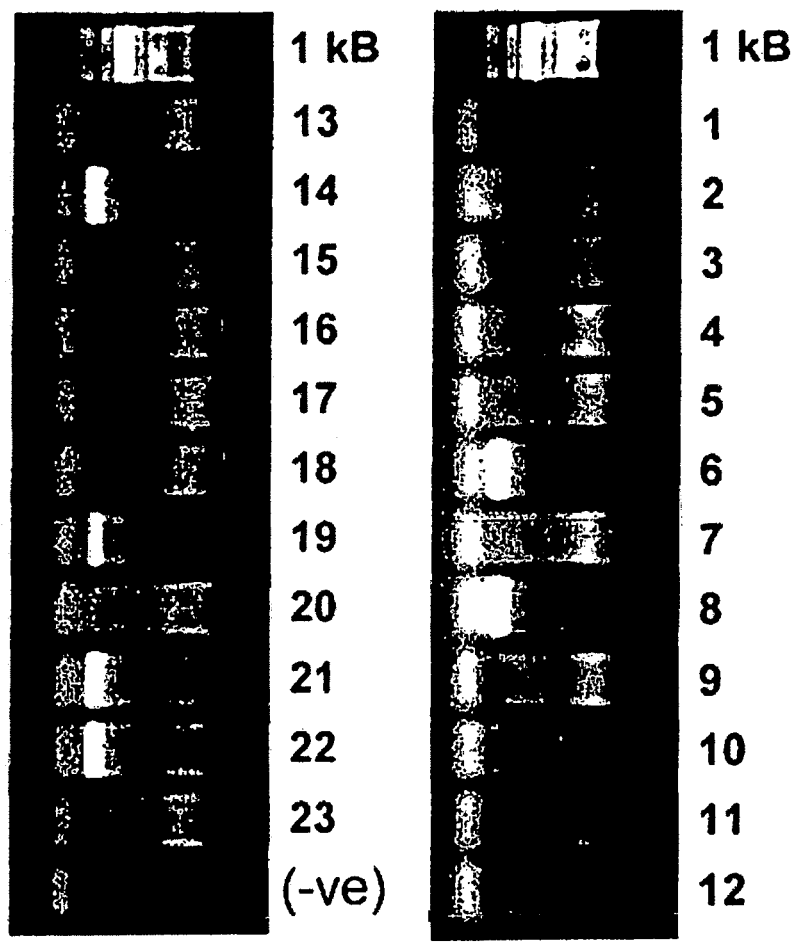
FIG. 10 illustrates the results from a PCR screen for integration of BAP-Enho1 into the genome of C57BL/6J pups (from injection of BAP-Enho1 into C57BL/6J oocytes) showing six pups out of 23 with integration of the transgene into the genome.

Transgenic strains over expressing Enho1 were generated using a construct (BAP-Enho1) containing the human β-actin promoter, a synthetic exon 1 and intron, and an open reading frame encoding the 76 aa Enho1 protein (FIG. 9A; see FIG. 4, the open reading frame is underlined). Eight founders were obtained (2 FVB/NJ, 6 C57BL/6J), with one of the FVB strains [FVB/NJ.Tg-(BAP-Enho1)AAB20], hereafter referred to as FVB.Tg, exhibiting an increase in hepatic Enho1 expression at 5-6 wk of age (FIG. 9B). FIG. 10 illustrates the results of PCR screening the pups in the first round of injection of BAP-Enho1 into C57BL/6J oocytes, showing six pups (6, 8, 14, 19, 21, and 22) with integration of the transgene into the genome.

At 5-6 wk of age, reductions in serum TG and TC are already evident in FVB.Tg (Table 5, FIG. 9C). Body weight (Table 5) and FM (FIG. 9D) of FVB.Tg transgenics was reduced relative to WT littermate. Weight gain of FVB.Tg mice was also reduced on HFD (60% kJ/fat), indicating protection from diet-induced obesity (FIG. 9E). Reduced body weight and fat content was still observed after 1 month on HFD, associated with a tendency for reduced fasting insulin levels of BAP-Enho1 transgenics compared to WT controls (180±60 vs. 310±40 pg/ml, 2-tailed Student's t-test P=0.085).

TABLE 5

Data from the first 3 litters of FVB.Tg mice.

| | Body weight (g) | Liver weight (g) | Liver as % of body weight | Glucose (mg/dL) | Triglyceride (mg/dL) | Cholesterol (mg/dL) |
|---|---|---|---|---|---|---|
| FVB WT | 20.5 ± 1.1 | 0.88 ± 0.01 | 4.3 ± 0.4 | 151 ± 14 | 105 ± 3 | 219 ± 7 |
| FVB.Tg | 17.8 ± 0.1* | 0.69 ± 0.01* | 3.9 ± 0.2 | 105 ± 6* | 82 ± 6* | 198 ± 4* |

All mice are female aged approximately 4.5 weeks, n = 3-5 per group.
*P < 0.05 compared to control group.

As shown above, it was observed that over expression of Enho1 impairs metabolic adaptation to fasting, perhaps indicating increased energy expenditure. To determine whether Enho1 increases energy expenditure, VO2 and RER was measured using indirect calorimetry (15,46,50). The Pennington Biomedical Research Center has a 16 chamber comprehensive laboratory animal monitoring system (CLAMS) housed in a temperature controlled incubator. The CLAMS simultaneously measured oxygen consumption (VO2), respiratory exchange ratio (RER, an indicator of whole animal substrate oxidation), physical activity in the X and Z axis, and food intake. Mice were placed in the CLAMS system, and the parameters indicated recorded for 72 h. Mice were fed ad libitum for 48 h, with a fast for final 24 h. The results for FVB.Tg are shown in FIGS. 13A-13F. Increased weight loss was observed after an overnight fast in obese KKAy, in obese B6 Ay/a mice expressing Ad5Enho1 (% weight loss after overnight fast for Ad5-Enho1 vs Ad5-GFP: 5.5±0.4% vs. 3.5±0.4%, P<0.01), and in 9 wk old lean FVB.Tg (13.6±1.1% vs. 10.0±0.7%, P<0.05). After 1 month of high fat feeding, measurement of energy metabolism by indirect calorimetry indicated significantly increased oxygen consumption (VO2 in ml/h: BAP-Enho1 Tg 4551±240, WT FVB 3807±145, P<0.05) and physical activity during lights off (X beam breaks per hour: BAP-Enho1 Tg 1431±181; WT FVB 2678±327, P<0.01). Increased energy expenditure may thus be a factor in the amelioration of diet-induced obesity and insulin resistance by Enho1.

Example 12

Enho1 Effects Adipocytes

An experiment was conducted to test the use of a recombinant or synthetic forms of the short secreted polypeptide Enho1$^{34-76}$ (SEQ ID NO:10). A study was conducted where the response of adipocytes and hepatocytes, two potential sites of Enho1 action, to synthetic Enho1$^{34-76}$ was analyzed with changes in extracellular regulated kinase (ERK) as the measured response. ERK1/2 and p38α are important in the regulation of lipolysis and thermogenesis in adipocytes.

Figures 11A, 11B:
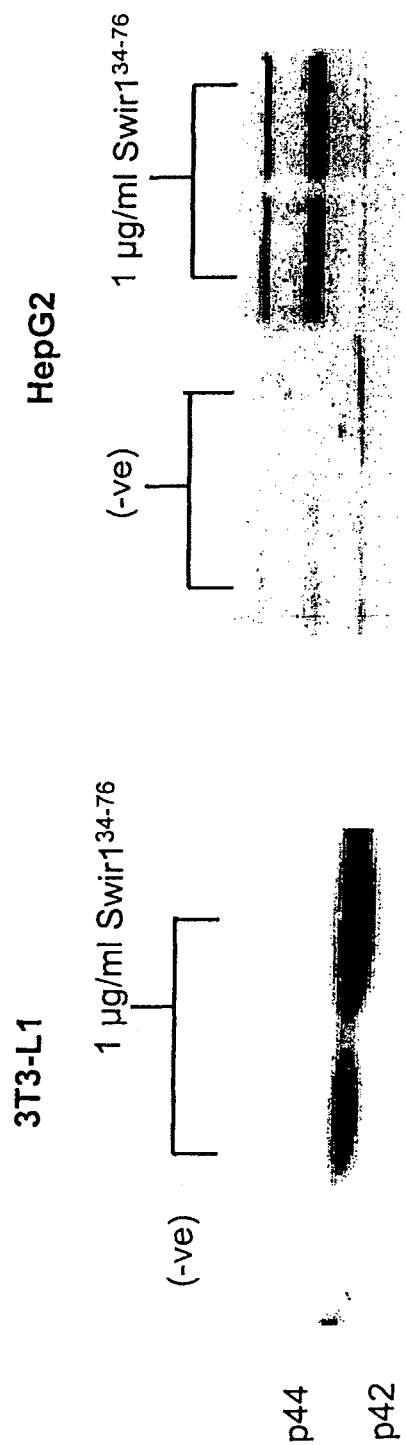
FIG. 11A illustrates the increase in Erk phosphorylation in 3T3-L1 adipocytes 15 minutes after the application of the secreted portion of protein Enho1 ($Enho1^{34-76}$; SEQ ID NO:10).
FIG. 11B illustrates the increase in Erk phosphorylation in HepG2 hepatocytes 15 minutes after the application of the secreted protein Enho1 ($Enho1^{34-76}$; SEQ ID NO:10).

Application of 1 μg/ml Enho1$^{34-76}$ was associated with a robust increase in the phosphorylation of Erk1 in fully differentiated 3T3-L1 adipocytes (FIG. 11A) and in HepG2 cells (FIG. 11B). These results indicate that functional receptors for Enho1$^{34-76}$ are active in adipocytes and hepatocytes, indicating that the synthetic peptide is biologically active. In addition, a shorter, second peptide was synthesized using amino acids 39 through 76 of SEQ ID NO:2, and called "Enho1$^{39-76}$" (SEQ ID NO:11). Similar results using adipocytes and hepatocytes were observed with this peptide. The loss of four amino acids did not appear to affect Enho1 function.

Example 13

Enho1 Function in Hypothalamus

Hypothalamic Enho1 may be involved in the regulation of energy homeostasis. Preliminary analysis using pAB1 demonstrated the presence of Enho1-immunoreactivity in neurons located in the arcuate nucleus of the hypothalamus (data not shown). It was predicted that a negative correlation exists between hypothalamic Enho1 expression and obesity and insulin resistance. In other words, reduced synthesis of Enho1 in liver and hypothalamus in situations of obesity may be a factor contributing to obesity and insulin resistance.

Figures 12A, 12B, 12C:
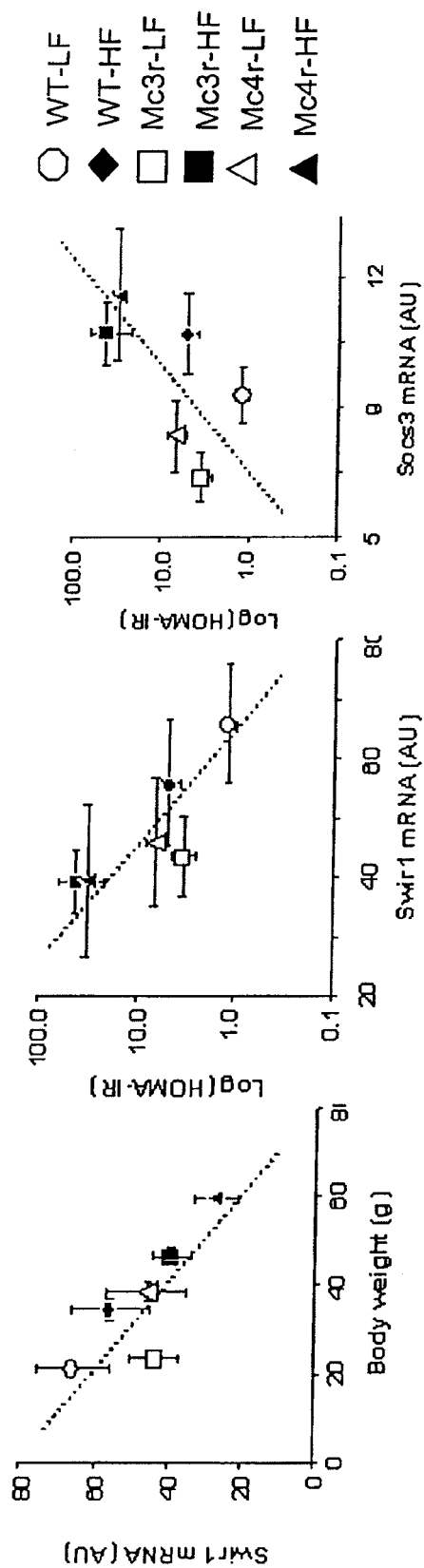
FIG. 12A illustrates the association between hypothalamic Enho1 mRNA expression and body weight in six-month-old mice from three strains (C57BL/6J(WT), Mc3rKO (Mc3r), or Mc4rKO (Mc4r) fed for three months on one of two diets (LF=10% kJ/fat; HF=60% kJ/fat).
FIG. 12B illustrates the association between hypothalamic Enho1 mRNA expression and HOMA-IR [(fasting insulin×glucose)/22.5] in six-month-old mice from three strains (C57BL/6J(WT), Mc3rKO (Mc3r), or Mc4rKO (Mc4r) fed for three months on one of two diets (LF=10% kJ/fat; HF=60% kJ/fat).
FIG. 12C illustrates the association between HOMA-IR [(fasting insulin×glucose)/22.5] and hypothalamic Socs3 (suppressor of cytokine signaling 3) mRNA expression in six-month-old mice from three strains (C57BL/6J(WT), Mc3rKO (Mc3r), or Mc4rKO (Mc4r) fed for three months on one of two diets (LF=10% kJ/fat; HF=60% kJ/fat).
Figure 13B:
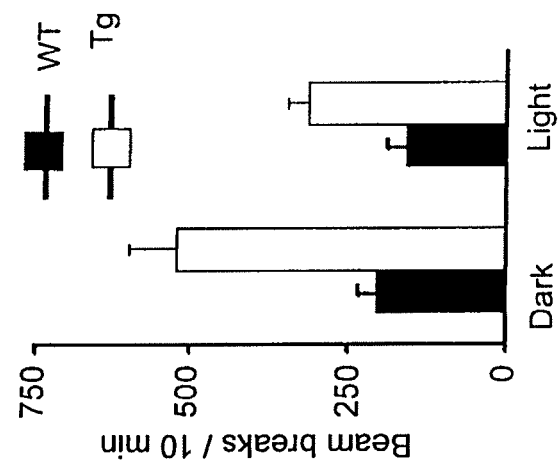
FIG. 13B illustrates the physical activity (measured in average number beam breaks/10 min for the period) in dark and light periods in wild-type (WT) and BAP-Enho1 transgenic mice (Tg) over a 24 hr.
Figure 13A:
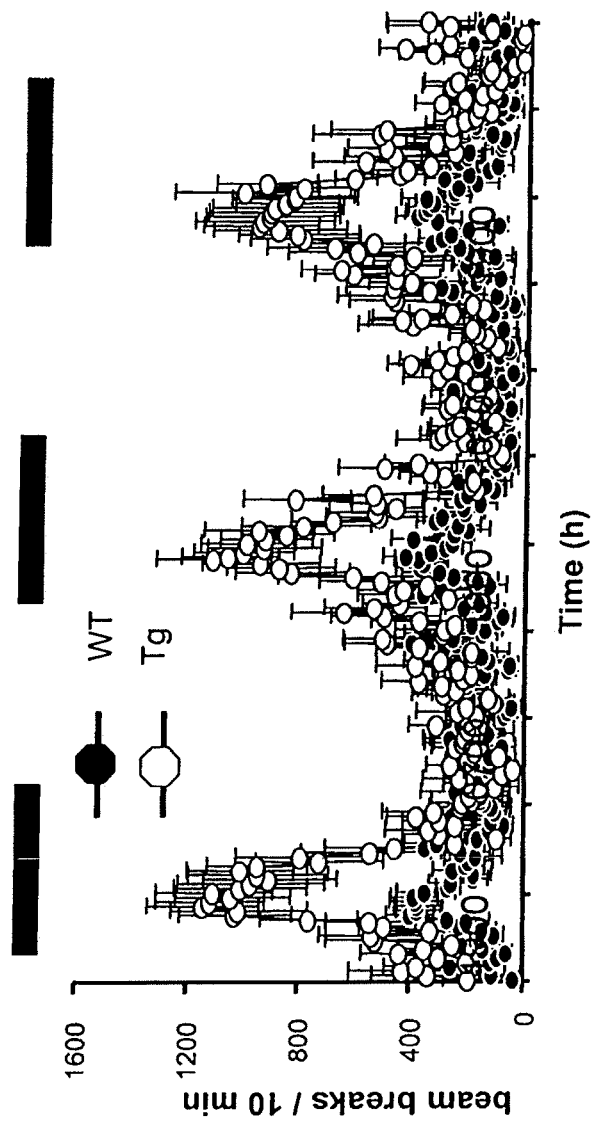
FIG. 13A illustrates the physical activity (measured in beam breaks/10 min) in wild-type (WT) and BAP-Enho1 transgenic mice (Tg) over 3 days.
Figure 13D:
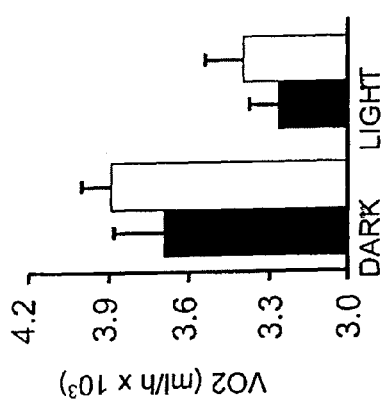
FIG. 13D illustrates the metabolic rate (measured as VO2 (ml/h×$10^3$)) in dark and light periods in wild-type (WT) and BAP-Enho1 transgenic mice (Tg) over a 24 hr.
Figure 13F:
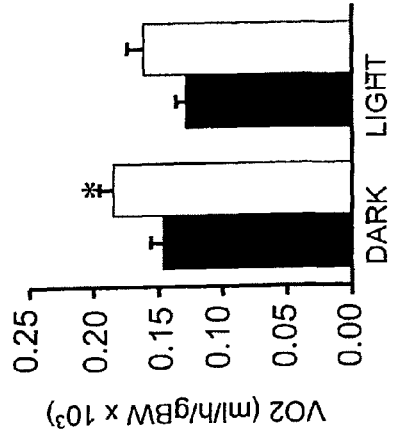
FIG. 13F illustrates the metabolic rate as a function of body weight (measured as VO2 (ml/h/gBW×$10^3$)) in dark and light periods in wild-type (WT) and BAP-Enho1 transgenic mice (Tg) over a 24 hr.
Figure 13C:
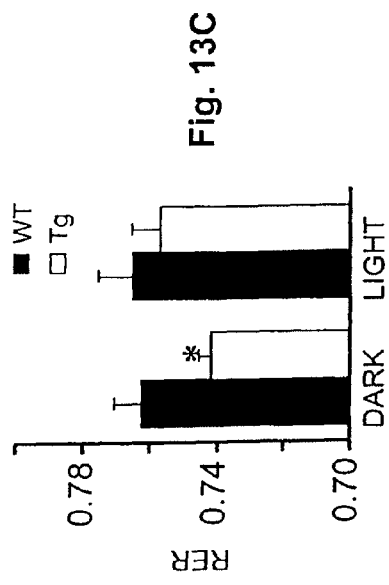
FIG. 13C illustrates whole body fat oxidation (RER) in dark and light periods in wild-type (WT) and BAP-Enho1 transgenic mice (Tg) over a 24 hr.
Figure 13E:
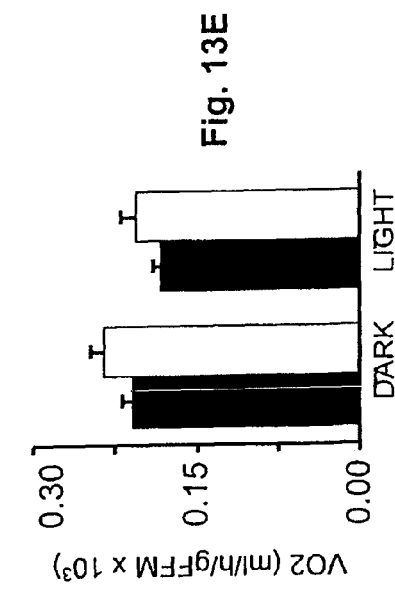
FIG. 13E illustrates the metabolic rate as a function of free fat mass (measured as VO2 (ml/h/gFFM×$10^3$)) in dark and light periods in wild-type (WT) and BAP-Enho1 transgenic mice (Tg) over a 24 hr.

Enho1 mRNA expression was measured by quantitative RT-PCR in mediobasal hypothalamic blocks from control (low fat diet) and diet-induced obese C57BL/6J, Mc3rKO and Mc4rKO mice (FIGS. 12A-12B). As predicted, Enho1 mRNA abundance in the hypothalamus was reduced in the obese state (FIG. 12A). Enho1 expression was also low in mice with elevated HOMA-IR values, an indicator of insulin resistance (FIG. 12B).

In contrast, Socs3 mRNA expression was elevated in situations of obesity and insulin resistance (FIG. 11C). This data indicates that reduced synthesis of Enho1 in situations of obesity is not be limited to the liver. Reduced Enho1 activity in the hypothalamus would also contribute to the development of obesity and insulin resistance.

In summary, an expression vector was constructed using a partial cDNA sequence encoding the predicted 76 residues of ENHO1 (between nucleotides 207 and 437 of BC021944), with an epitope-tag inserted onto the carboxyterminal end to allow visualization of the protein on western blot using a commercially available antibody. Using this construct, it was verified that the reported sequences encoded a secreted protein. This expression vector and an expression vector encoding the native protein without an epitope label were then used to construct a recombinant adenovirus (Ad5-ENHO1) for use in mouse studies. Injections of 5×10$^8$ pfu of the adenovirus into the tail vein resulted primarily in infection of the liver, and to a lesser extent, the spleen. Using the adenovirus expressing the epitope-tagged ENHO1, it was demonstrated that 5 days after injection of the virus, there was wide spread distribution of ENHO1 protein in liver, brain, and skeletal muscle. Using this adenovirus expressing the native form of ENHO1, a new function (reduction of fasting serum triglyceride and cholesterol) was shown for the secreted protein. A reduction in liver ENHO1 mRNA expression was observed in obese mice with hyperlipidemia, with the magnitude of the reduction correlating with the increase of total cholesterol and triglyceride. Using the adenovirus expressing the native form of ENHO1, it was shown that increasing the expression of the mRNA encoding the ENHO1 protein in mouse models of obesity with high cholesterol and triglycerides was effective at reducing both cholesterol and triglycerides toward normal levels. The effects of Ad5-ENHO1 infection to reduce triglyceride and total cholesterol were reproducible, being observed in three different mouse strains ($Lep^{ob}/Lep^{ob}$, $KKA^y$, and C57BL/6J). In some mice, an improvement in insulin sensitivity was observed in a trend of lower fasting insulin and glucose and an improvement in glucose tolerance test results. The latter observations suggested that ENHO1 may also be effective at improving insulin sensitivity in an obese, insulin-resistant patient.

The data strongly suggest that full-length Swirl peptide (SEQ ID NO:2), or peptide derivatives, homologues, analogues, or mimetics thereof, delivered by oral intake, injection, subcutaneous patch, or intranasal routes, could be used as therapeutic or diagnostic agents for hypercholesterolemia, hypertriglyceridemia, insulin resistance, obesity, diabetes, and/or energy imbalance. By methods known in the art, substitutions within the native coding sequence can be made to make derivatives of Swirl with increased stability and/or biological potency. Moreover, the Swirl peptide can be used to identify its cell receptor which can then be used as as-yet-unidentified receptor(s) for Swirl is (are) a potential drug target(s) for the development of therapies aimed at reducing total cholesterol, triglycerides, insulin resistance, obesity, diabetes and/or energy imbalance.

A novel secreted protein, Enho1, that is an important factor in the etiology of insulin resistance and hepatic steatosis in the obese state has been identified by Microarray analysis of gene expression in mouse models of moderate- to severe-diabesity. Enho1 significantly reduces HOMA-IR, an index of fasting insulin and glucose, and serum lipids in mouse models of type 2 diabetes, and significantly reduces hepatic lipids indicating a reversal of hepatic steatosis. Transgenic over expression of Enho1 is associated with a lean phenotype. Enho1 may act in a manner similar to leptin and adiponectin, improving metabolic profile in the obese insulin state by stimulating energy expenditure and increasing oxidative metabolism.

Example 14

Enho1 Treatment Will Reverse Hepatic Insulin Resistance

Preliminary data from Ad5-Enho1 and BAP-Enho1 transgenics (shown above) indicate improved insulin action and lipid metabolism. In FVB.Tg mice, increased oxidative metabolism is a likely factor explaining these effects. It may not be possible to dissect the anti-diabetc actions of Enho1 from those secondary to reductions of FM. Preliminary data using recombinant adenovirus indicate that Enho1 reduces hyperinsulinemia and hyperlipidemia independently of effects on obesity. Further experiments using recombinant adenovirus and synthetic peptide may therefore provide important information regarding 'direct' effects of Enho1 on liver metabolism and insulin sensitivity.

Experiments will be conducted to determine whether the reversal of hepatic steatosis with Ad-Enho1 treatment is associated with improved insulin sensitivity in liver and skeletal muscle by measuring insulin receptor signaling. These will include analysis of insulin receptor substrates 1 and 2 phosphorylation, which are distal to the insulin receptor tyrosine kinase. Activity of protein kinase B (PKB)/Akt, a serine/threonine kinase involved in regulating glucose transport that is downstream of phosphatidyl-3' kinase (44,45), will also be measured as an indicator of insulin receptor activation. Pilot data showing significantly greater weight loss of mice infected with Ad5-Enho1 suggests increased basal metabolic rate. Whether Ad5-Enho1 increases whole body metabolic rate during postprandial and fasting states will be determined using indirect calorimetry, and oxidative metabolism in tissue lysates from liver, skeletal muscle and brown adipose tissue shall be determined.

The basic protocol for adenovirus treatment is shown in FIG. 7C. Briefly, all mice will have $5\times10^9$ pfu of Ad5-ENHO1 or Ad5-GFP injected into the tail vein (n=12/group, 24 total). Mice shall be allowed 4 d to recover before use in the following experiments. A liver sample taken at termination will be used to estimate infection by measuring Enho1 mRNA by RealTime PCR and Northern blot analysis. In preliminary experiments, a 4-fold increase in Enho1 mRNA was observed 4-7 d post infection. Enho1 protein shall also be measured either by Western blot, or through the use of assays (RIA/ELISA) currently under development. Mice shall be weighed on the day of adenovirus injection, and pre- and post-fasting. If possible, body composition shall be determined using nuclear magnetic resonance (NMR) (15,32,46). Mice shall be acclimated to housing in wire-mesh caging that allows for measurement of food intake and spillage, as previously described (15).

If the sexual dimorphic phenotype of the FVB.Tg is reproducible and observed in BAP-Enho1 transgenics on the C57BL/6J background, the Ad5 experiments will be modified to investigate the response of males and females. Most of the experiments investigating the response of obese insulin resistant mice to Ad5-Enho1 treatment used males; it may be that females will exhibit a different response, perhaps exhibiting weight loss in addition to improved insulin sensitivity. This would not be unprecedented, for example sexual dimorphism has been observed in the response of male and female rats to the anorectic actions of insulin and leptin (47,48).

Determine Whether Reversal of Hepatic Steatosis is Associated with Increased Insulin Sensitivity.

This experiment will involve KKAy and Ay/a mice, with two groups of twelve within genotype (Ad5-Enho1, Ad5-GFP controls) (24 KKAy, 24 Ay/a). On day 5 after an overnight fast, six of the Ad5-ENHO1 and Ad5-GFP groups shall be administered a single intraperitoneal of insulin (1 U/kg), with the remaining six receiving saline. Mice shall be euthanized either 10 or 20 minutes (n=3/group) post injection, and tissue samples collected (liver, quadriceps muscle) and snap frozen on liquid nitrogen. IRS phosphorylation, PKB activity, and FoxO1 phosphorylation shall be measured as previously described (15,49). This experiment shall be repeated two more times with only 8 mice per group to do insulin and glucose tolerance tests.

It is predicted that the anti-steatotic effect of Ad5-ENHO1 will increase insulin-stimulated activity of the insulin receptor tyrosine kinase cascade in liver. Ad5-ENHO1 may also improve insulin signaling in muscle and/or adipose tissue. The initial studies investigating glucose clearance resulted in mixed results (data not shown), perhaps due to sub-optimal experimental design [i.e., small numbers of mice (n=4-5); performed at variable times (up two two weeks) after adenovirus injection]. It is predicted that Ad5-Enho1 will improve glucose clearance in response to glucose/insulin injections.

Determine Whether Enho1 Increases Whole Body Energy Expenditure and Oxidative Metabolism.

To determine whether hepatic expression of Enho1 increases energy expenditure, VO2 and RER of obese Ay/a and lean and diet-induced obese C57BL/6J mice infected with Ad5-Enho1 or Ad5-GFP (n=8/group) shall be measured using indirect calorimetry (15,46,50). The Pennington Biomedical Research Center has a 16 chamber comprehensive laboratory animal monitoring system (CLAMS) housed in a temperature controlled incubator. The CLAMS simultaneously measures oxygen consumption (VO2), respiratory exchange ratio (RER, an indicator of whole animal substrate oxidation), physical activity in the X and Z axis, and food intake. Mice shall be placed in the CLAMS system 96 h after adenovirus injection, and the parameters indicated recorded for 72 h. Mice shall be allowed to feed ad libitum for 48 h, with a fast for final 24 h. In a separate experiments, fatty acid oxidation ($C^{14}$-palmitate) and mitochondrial enzyme function (citrate synthase activity, cytochrome c oxidase) will be measured in liver, gastrocnemius, and brown adipose tissue collected from Ay/a and C57BL/6J mice infected with Ad5-Enho1 or Ad5-GFP (n=8/group). A portion of liver shall be collected and snap frozen for measurement of mRNA and protein expression of transcription factors (i.e., SREBP1c, PPARγ) and enzyme involved in lipogenesis (32).

The increased weight loss of mice infected with Ad5-Enho1 indicates increased basal metabolic rate, a finding corroborated by fasting weight loss and indirect calorimetry data from BAP-Enho1 transgenics. (See FIGS. 13A-F) It is predicted that infection with Ad5-Enho1 will increase VO2, although this may only be evident during the fasting phase. An increase in mitochondrial oxidative enzyme activity in liver only would be consistent with Enho1 acting as an autocrine/paracrine factor. Increased mitochondrial oxidative enzyme activity in skeletal muscle and brown adipose tissue would suggest an endocrine function, either acting through the autonomic nervous system or through receptors expressed in muscle and/or brown adipose tissue. If Ad5-Enho1 is markedly increasing energy expenditure (as observed in FVB.Tg) but is not affecting body weight, then a compensatory increase in food intake would be predicted. A reduction in the expression of genes involved in lipogenesis, as observed in OBOB mice treated with Ad5-Enho1, is also predicted. (FIG. 8A-8D).

Example 15

Transgenic Expression of Enho1 Prevents Obesity and Insulin Resistance

Transgenic mice over expressing leptin (51,52) and adiponectin (53,54) have demonstrated the anti-diabetic action of over expression of either protein. It is expected that over expression of Enho1 will have outcomes comparable to that observed with over expression of adiponectin and leptin; i.e. improved insulin sensitivity and glucose tolerance, and lower fasting lipids in situations of diet- and genetically induced obesity. It is also predicted that Enho1 will increases energy expenditure by increasing oxidative metabolism in liver, skeletal muscle, and/or brown adipose tissue. A comprehensive analysis of the physiology of Enho1 action is important for future experiments that focus on the mechanism(s) by which this polypeptide regulates energy metabolism and insulin signaling.

Transgenics:

A sequence encoding the 76 aa protein has been ligated into a synthetic transgene controlled by the human β-actin promoter (BAP) (FIG. 9A). Enho1 is a secreted polypeptide (FIG. 4), and thus tissue-selectivity is not important for these transgenic studies. Promoters specific for tissues have not been used where the endogenous gene is abundantly expressed, because suppression of the endogenous gene may limit efficacy of over expression (53,54). A comprehensive analysis of mRNA expression shall be completed using quantitative RT-PCR (qRT-PCR) as previously described (31,32, 46) and Northern blot analysis. Protein levels shall be measured by Western blot using the two polyclonal antibodies against the N- and C-terminus of $Enho^{34-76}$ (pAB1, pAB2) (FIG. 5). This may require using immunoprecipitation to detect protein. Alternatively, if antibodies in hand or in development are useful for developing sensitive and quantitative assays, then these shall be used. Transgene copy number shall be determined by Southern blot analysis. A sub-aim of this experiment is therefore a more comprehensive analysis of Enho1 mRNA expression in mouse tissues (liver, hypothalamus, forebrain, hindbrain, skeletal and cardiac muscle, retroperitoneal and inquinal adipose depots, stomach, intestine, pancreas, kidney). Major organs (heart, kidney, gut, liver) shall be weighed and inspected histologically for major morphological changes.

We have shown that Enho1 is one of a small group of secreted polypeptides (leptin, adiponectin) that, when over expressed, improves metabolic profile (i.e. increased insulin sensitivity, reduced hepatic lipogenesis) in mouse models of obesity and insulin resistance. The over expression of Enho1 has leptin-like effects on energy metabolism, protecting against diet-induced obesity and insulin resistance. Administering Enho1 can reverse insulin resistance and dyslipidemia associated with diet- and genetically-induced obesity, and can prevent or delay onset of diabesity.

Examples 16 to 25 were carried out using human Enho 1, a 76 amino acid peptide having the sequence:

```
                                          (SEQ ID NO: 14)
MGAAISQGALIAIVCNGLVGFLLLLLWVILCWACHSRSADVDSLSESS
PNSSPGPCPEKAPPPPQKSHEGSYLLQP
```

Statistical analysis of the results was carried out using ANOVA analysis tools with post hoc tests. Data are reported as the mean±standard error (SE).

Of course, the skilled artisan would know and realize that experiments similar to those described herein may be carried out to determine the effect of Enho-1 upon various parameters of metabolism such as weight loss, hepatic steatosis, lipids and triglycerides, glucose, insulin levels and the like. For example, the length of treatment time may be varied, the genetic make up of the mice or rat strains may be different, different diet regimes may be applied, etc. These experiments are in no way intended to be binding and are representative of those which are useful to study the effects of peptides such as Enho-1 in mammals.

Example 16

Effect of Enho 1 on Weight Loss (Short-Term Treatment)

The effect of Enho-1 upon weight loss was tested over the course of 3 days using KKAy mice. The mice were fed Breeder Chow (Purina 5015) and were approximately 12-14 weeks of age at the start of the experiment. Six control mice received vehicle only while six test mice each received doses of either 900 nmol/kg/d or 9000 nmol/kg/d. The injections were given as 3 intraperitoneal (ip) injections at 0600, 1400 and 2000 h on days 1 and 2; over the 3 day period, the mice received a total of 7 injections. All animals were euthanized 5 hours after the last injection given the morning of the third day. Food was removed after the final injection.

The six control mice had a mean pre-treatment weight of 35.3 g (SE±1.2 g) and a mean post-treatment weight of 33.6 g (SE±1.0). The difference of −1.7 g (SE±0.3) represents a −4.8% (SE±0.6) reduction in weight.

The six test mice which received 900 nmol/kg/d of Enho 1 had a pre-treatment weight of 35.3 g (SE±1.1) and post-treatment weight of 33.0 g (SE±1.0). The difference of −2.3 g (SE±0.2) represents a −6.5% (SE±0.6) reduction in weight.

The six test mice which received 9000 nmol/kg/d of Enho 1 had a pre-treatment weight of 35.6 g (SE±0.6) and post-treatment weight of 33.1 g (SE±0.4). The difference of −2.6 g (SE±0.3) represents a −7.1% (SE±0.8) reduction in weight.

These results are reported in Table 6.

TABLE 6 the effect of Enho-1 upon weight loss

|  | Control | 900 nmol/kg/d | 9000 nmol/kg/d |
|---|---|---|---|
| Weight (pre-treatment) | 35.3 ± 1.2 g | 35.3 ± 1.1 | 35.6 ± 0.6 |
| Weight (termination) | 33.6 ± 1.0 | 33.0 ± 1.0 | 33.1 ± 0.4 |
| Delta body weight |  |  |  |
| Grams | −1.7 ± 0.3 | −2.3 ± 0.2 | −2.6 ± 0.3 |
| % | −4.8 ± 0.6 | −6.5 ± 0.6 | −7.1 ± 0.8 |

P = 0.073 ANOVA

Example 17

Effect of Enho 1 on Insulin and Glucose Levels

The effect of Enho-1 upon insulin and glucose was tested over the course of 3 days using KKAy mice. The mice were fed Breeder Chow (Purina 5015) and were approximately 12-14 weeks of age at the start of the experiment. Six control mice received vehicle only while five or six test mice each received doses of either 900 nmol/kg/d or 9000 nmol/kg/d, respectively. The injections were given as 3 ip injections at 0600, 1400 and 2000 h on days 1 and 2; over the 3 day period, the mice received a total of 7 injections. All animals were euthanized 5 hours after the last injection given the morning of the third day. Food was removed after the final injection. The HOMA-IR for each treatment was calculated using the following formula:

$$((\text{glucose mg/dL} \div 18) \times (\text{insulin ng/ml} \times 25.05)) \div 22.5$$

The six control mice demonstrated a post-test mean blood glucose level of 524 mg/dL (SE±48) and an insulin level of 7.4 ng/ml (SE±0.6); the HOMA-IR value for the control group was determined to be 234 (SE±16).

The five test mice which received 900 nmol/kg/d of Enho 1 demonstrated a post-test mean blood glucose level of 474 mg/dL (SE±29) and an insulin level of 5.7 ng/ml (SE±0.5); the HOMA-IR value for this group was determined to be 167 (SE±18), representing a decrease of 29% as compared to the control group. The blood glucose levels decrease by approximately 10% while the insulin levels were reduced by about 22%.

The six test mice which received 9000 nmol/kg/d of Enho 1 demonstrated a post-test mean blood glucose level of 480 mg/dL (SE±38) and an insulin level of 7.0 ng/ml (SE±0.8); the HOMA-IR value for this group was determined to be 213 (SE±37), representing a decrease of 9% as compared to the control group.

These results are reported in Table 7.

TABLE 7 the effect of Enho-1 upon insulin and glucose

|  | Control | 900 nmol/kg/d | 9000 nmol/kg/d |
|---|---|---|---|
| Blood glucose (mg/dL) | 524 ± 48 | 474 ± 29 | 480 ± 38 |
| Insulin (ng/ml) | 7.4 ± 0.6 | 5.7 ± 0.5 | 7.0 ± 0.8 |
| HOMA-IR | 234 ± 16 | 167 ± 18 (↓ 29%) | 213 ± 37 (↓ 9%) |

Example 18

Effect of Enho 1 on Hepatic Steatosis

The effect of Enho-1 upon liver weight, liver lipid content and liver TG was tested over the course of 3 days using KKAy mice. The mice were fed Breeder Chow (Purina 5015) and were approximately 12-14 weeks of age at the start of the experiment. Six control mice received vehicle only while five or six test mice each received doses of either 900 nmol/kg/d or 9000 nmol/kg/d, respectively. The injections were given as 3 ip injections at 0600, 1400 and 2000 h on days 1 and 2; over the 3 day period, the mice received a total of 7 injections. All animals were euthanized 5 hours after the last injection given the morning of the third day. Food was removed after the final injection.

The six control mice exhibited a mean liver weight of 1.6 g (SE±0.1), representing 4.6% (SE±0.2) of total body weight. The mean liver lipid level for the control group was 94 mg/g (SE±6), with total lipids measuring 147 mg/g (SE±14). Liver TG for the control group was determined to be 59 mg/g (SE±5; P<0.05) while the total liver TG was determined to be 92 mg/g (SE±10; p=0.062).

The five test mice which received 900 nmol/kg/d of Enho 1 demonstrated a post-test mean liver weight of 1.6 g (SE±0.1), representing 5.0% (SE±0.2) of body weight. The mean liver lipid level for this group was determined to be 82 mg/g (SE±9), with total lipids measuring 137 mg/g (SE±18). Liver TG for this group was determined to be 40 mg/g (SE±8; P<0.05) while the total liver TG was determined to be 66 mg/g (SE±13; p=0.062).

The six test mice which received 9000 nmol/kg/d of Enho 1 demonstrated a post-test mean liver weight of 1.6 g (SE±0.1), representing 4.9% (SE±0.3) of body weight. The mean liver lipid level for this group was determined to be 87 mg/g (SE±6), with total lipids measuring 143 mg/g (SE±17). Liver TG for this group was determined to be 32 mg/g (SE±5; P<0.05) while the total liver TG was determined to be 53 mg/g (SE±11; p=0.062).

These data show that Enho 1 is capable of inducing a dose-dependent reversal of hepatic steatosis. In mice receiving the 900 nmol/kg/d and the 9000 nmol/kg/d dosage, the livers, the TG was reduced by 32% and 46%, respectively, as compared to the control group.

These results are reported in Table 8.

TABLE 8 the effect of Enho-1 upon liver weight, liver lipid content and liver TG

|  | Control | 900 nmol/kg/d | 9000 nmol/kg/d |
|---|---|---|---|
| Liver weight | | | |
| (g) | 1.6 ± 0.1 | 1.6 ± 0.1 | 1.6 ± 0.1 |
| % body weight | 4.6 ± 0.2 | 5.0 ± 0.2 | 4.9 ± 0.3 |
| Liver lipid | | | |
| mg/g | 94 ± 6 | 82 ± 9 | 87 ± 6 |
| total | 147 ± 14 | 137 ± 18 | 143 ± 17 |
| Liver TG | | | |
| mg/g | 59 ± 5 | 40 ± 8 | 32 ± 5 |
| P < 0.05 ANOVA | | | P < 0.05 vs control |
| total | 92 ± 10 | 66 ± 13 | 53 ± 11 |
| P = 0.062 ANOVA | | | |

Example 19

Effect of Enho 1 on Weight Loss (Short Term) in Obese Mice

The effect of Enho-1 upon weight loss was tested over the course of 3 days using diet induced obese (DIO) C57BL/6J mice (Jackson Laboratories, Bar Harbor, Me.). The mice were fed Research Diets 12492 (60% kJ/fat) for 12 weeks, resulting in obesity and moderate hyperglycemia in the animals. The mice were approximately 20-22 weeks of age and 30-50 g in weight at the start of the experiment. Fasting blood glucose was determined to be approximately 170-220 mg/dL. Six control mice received vehicle only while six test mice each received doses of either 90 nmol/kg/d, 900 nmol/kg/d or 9000 nmol/kg/d. The injections were given as 3 ip injections at 0600, 1400 and 2000 h on days 1 and 2; over the 3 day period, the mice received a total of 7 injections. All animals were euthanized 5 hours after the last injection given the morning of the third day. Food was removed after the final injection.

The six control mice exhibited mean pre- and post-treatment weights of 42.7 g (SE±2.4 g) and 41.7 g (SE±2.3), respectively, representing a 2.4% (SE±0.5) reduction in total body weight.

The six test mice receiving 90 nmol/kg/d Enho 1 exhibited mean pre- and post-treatment weights of 42.9 g (SE±1.2) and 41.7 g (SD±0.9), respectively, representing a 2.9% (SE±0.6) reduction in total body weight.

The six test mice receiving 900 nmol/kg/d Enho 1 exhibited mean pre- and post-treatment weights of 42.8 g (SE±2.9) and 41.3 g (SE±2.7), respectively, representing a 3.5% (SE±0.7) reduction in total body weight.

The six test mice receiving 9000 nmol/kg/d Enho 1 exhibited mean pre- and post-treatment weights of 42.7 g (SE±1.6) and 40.9 g (SE±1.6), respectively, representing a 4.1% (SE±0.6) reduction in total body weight.

These results are reported in Table 9.

TABLE 9 the effect of Enho-1 upon weight loss

|  | Control | 90 nmol/kg/d | 900 nmol/kg/d | 9000 nmol/kg/d |
|---|---|---|---|---|
| Weight (pre-treatment) | 42.7 ± 2.4 | 42.9 ± 1.2 | 42.8 ± 2.9 | 42.7 ± 1.6 |
| Weight (termination) | 41.7 ± 2.3 | 41.7 ± 0.9 | 41.3 ± 2.7 | 40.9 ± 1.6 |
| Delta body weight | | | | |
| Grams | −1.0 ± 0.2 | −1.3 ± 0.3 | −1.5 ± 0.3 | −1.7 ± 0.2 |
| % | −2.4 ± 0.5 | −2.9 ± 0.6 | −3.5 ± 0.7 | −4.1 ± 0.6 |

Example 20

Effect of Enho 1 on Insulin and Glucose Levels

The effect of Enho-1 upon insulin and glucose was tested over the course of 3 days using diet induced obese (DIO) C57BL/6J mice (Jackson Laboratories, Bar Harbor, Me.). The mice were fed Research Diets 12492 (60% kJ/fat) for 12 weeks, resulting in obesity and moderate hyperglycemia in the animals. The mice were approximately 20-22 weeks of age and 30-50 g in weight at the start of the experiment. Fasting blood glucose was determined to be approximately 170-220 mg/dL. Six control mice received vehicle only while six test mice each received doses of either 90 nmol/kg/d, 900 nmol/kg/d or 9000 nmol/kg/d. The injections were given as 3 ip injections at 0600, 1400 and 2000 h on days 1 and 2; over the 3 day period, the mice received a total of 7 injections. All animals were euthanized 5 hours after the last injection given the morning of the third day. Food was removed after the final injection.

The HOMA-IR for each treatment was calculated using the following formula:

$$((glucose\ mg/dL \div 18) \times (insulin\ ng/ml \times 25.05)) \div 22.5$$

The six control mice demonstrated a post-test mean blood glucose level of 196 mg/dL (SE±7) and an insulin level of 4.8 ng/ml (SE±0.2); the HOMA-IR value for the control group was determined to be 59 (SE±3; p=0.065).

The six test mice which received 90 nmol/kg/d of Enho 1 demonstrated a post-test mean blood glucose level of 204 mg/dL (SE±7) and an insulin level of 3.8 ng/ml (SE±0.4); the HOMA-IR value for this group was determined to be 50 (SE±5), representing a decrease of 15% as compared to the control group.

The six test mice which received 900 nmol/kg/d of Enho 1 demonstrated a post-test mean blood glucose level of 166 mg/dL (SE±13; P>0.05) and an insulin level of 4.2 ng/ml (SE±0.5); the HOMA-IR value for this group was determined to be 42 (SE±3), representing a decrease of 29% (p<0.02) as compared to the control group. The blood glucose levels decreased by approximately 15% while the insulin levels were reduced by about 14%.

The six test mice which received 9000 nmol/kg/d of Enho 1 demonstrated a post-test mean blood glucose level of 198 mg/dL (SE±9) and an insulin level of 4.2 ng/ml (SE±0.3); the HOMA-IR value for this group was determined to be 52 (SE±4), representing a decrease of 12% as compared to the control group.

These results are reported in Table 10.

TABLE 10 the effect of Enho-1 upon insulin and glucose

|  | Control | 90 nmol/kg/d | 900 nmol/kg/d | 9000 nmol/kg/d |
|---|---|---|---|---|
| Blood glucose (mg/dL) $p < 0.05$ ANOVA | 196 ± 7 | 204 ± 7 | 166 ± 13 $P < 0.05$ vs 90 | 198 ± 9 |
| Insulin (ng/ml) | 4.8 ± 0.2 | 3.8 ± 0.4 | 4.2 ± 0.5 | 4.2 ± 0.3 |
| HOMA-IR 1-way ANOVA $p = 0.065$ | 59 ± 3 | 50 ± 5 (↓ 15%) | 42 ± 3 (↓ 29%) | 52 ± 4 (↓ 12%) |

Example 21

Effect of Enho 1 on Hepatic Steatosis

The effect of Enho-1 upon liver weight, liver lipid content and liver TG was tested over the course of 3 days using diet induced obese (DIO) C57BL/6J mice (Jackson Laboratories, Bar Harbor, Me.). The mice were fed Research Diets 12492 (60% kJ/fat) for 12 weeks, resulting in obesity and moderate hyperglycemia in the animals. The mice were approximately 20-22 weeks of age and 30-50 g in weight at the start of the experiment. Fasting blood glucose was determined to be approximately 170-220 mg/dL. Six control mice received vehicle only while six test mice each received doses of either 90 nmol/kg/d, 900 nmol/kg/d or 9000 nmol/kg/d. The injections were given as 3 ip injections at 0600, 1400 and 2000 h on days 1 and 2; over the 3 day period, the mice received a total of 7 injections. All animals were euthanized 5 hours after the last injection given the morning of the third day. Food was removed after the final injection.

The six control mice exhibited a mean liver weight of 1.6 g (SE±0.2), representing 3.7% (SE±0.2) of total body weight. The mean liver lipid level for the control group was 155 mg/g (SE±39), with total lipids measuring 272 mg/g (SE±89). Liver TG for the control group was determined to be 58 mg/g (SE±11) while the total liver TG was determined to be 87 mg/g (SE±15).

The six test mice which received 90 nmol/kg/d of Enho 1 demonstrated a post-test mean liver weight of 1.5 g (SE±0.0), representing 3.6% (SE±0.1) of body weight. The mean liver lipid level for this group was determined to be 126 mg/g (SE±9), with total lipids measuring 188 mg/g (SE±13). Liver TG for this group was determined to be 57 mg/g (SE±8) while the total liver TG was determined to be 86 mg/g (SE±14).

The six test mice which received 900 nmol/kg/d of Enho 1 demonstrated a post-test mean liver weight of 1.5 g (SE±0.2), representing 3.5% (SE±0.2) of body weight. The mean liver lipid level for this group was determined to be 137 mg/g (SE±34), with total lipids measuring 226 mg/g (SE±77). Liver TG for this group was determined to be 48 mg/g (SE±12) while the total liver TG was determined to be 66 mg/g (SE±14).

The six test mice which received 9000 nmol/kg/d of Enho 1 demonstrated a post-test mean liver weight of 1.4 g (SE±0.2), representing 3.4% (SE±0.3) of body weight. The mean liver lipid level for this group was determined to be 139 mg/g (SE±42), with total lipids measuring 230 mg/g (SE±96). Liver TG for this group was determined to be 47 mg/g (SE±9) while the total liver TG was determined to be 63 mg/g (SE±10).

These data show that Enho 1 is capable of inducing a dose-dependent reversal of hepatic steatosis. In mice receiving the 9000 nmol/kg/d dosage, the livers, the liver TG was reduced by 18-19% while serum TG was reduced by 20% ($p<0.05$; 1-tailed t-test) as compared to the control group.

These results are reported in Table 11.

TABLE 11

The effect of Enho-1 upon liver weight, liver lipid content and liver TG

|  | Control | 90 nmol/kg/d | 900 nmol/kg/d | 9000 nmol/kg/d |
|---|---|---|---|---|
| Liver weight |  |  |  |  |
| grams | 1.6 ± 0.2 | 1.5 ± 0.0 | 1.5 ± 0.2 | 1.4 ± 0.2 |
| % body weight | 3.7 ± 0.2 | 3.6 ± 0.1 | 3.5 ± 0.2 | 3.4 ± 0.3 |
| Liver lipid |  |  |  |  |
| mg/g | 155 ± 39 | 126 ± 8 | 137 ± 34 | 139 ± 42 |
| total | 272 ± 89 | 188 ± 13 | 226 ± 77 | 230 ± 96 |
| Liver TG |  |  |  |  |
| mg/g | 58 ± 11 | 57 ± 8 | 48 ± 12 | 47 ± 9 |
| total | 87 ± 14 | 86 ± 14 | 66 ± 14 | 63 ± 10 |

Example 22

Effect of Enho 1 on Serum Lipids

The effect of Enho-1 upon liver serum lipid content was tested over the course of 8 days using obese (ob/ob) mice. The mice were fed Research Diets 12450 and were approximately 9-10 weeks of age at the start of the experiment. Control mice received vehicle only while test mice each received doses of either 90 nmol/kg/d, 900 nmol/kg/d or 9000 nmol/kg/d. The injections were given as 3 ip injections at 0800, 1200 and 1600 h for 7 days. On day 8, the mice were given the 0800 h injection and were sacrificed 1-3 h later, at which time blood samples were taken.

Blood glucose levels were measured using an Accu-Chek glucometer. Insulin levels were measured by ELISA (Mercodia Mouse Insulin ELISA, ALPCO) while triglycerides were measured using a Triglyceride L-Type TG H kit (Wako Diagnostics).

Eight control mice exhibited a mean blood triglyceride level of 29.6 mg/dL (SE±5.9).

Eight test mice which received 90 nmol/kg/d of Enho 1 demonstrated a post-test blood TG level of 19.4 mg/dL (SE±2.2), a decrease of 34% in comparison with the control.

Seven test mice which received 900 nmol/kg/d of Enho 1 demonstrated a post-test blood TG level of 18.4 mg/dL (SE±2.3), a decrease of 38% from the control.

The final group of seven mice which received 9000 nmol/kg/d of Enho 1 demonstrated a post-test blood TG level of 22.0 mg/dL (SE±2.2), a decrease of 26% from the control.

These results are reported in Table 12.

TABLE 12

The effect of Enho-1 upon liver serum lipid content

|  | Control | 90 nmol/kg/d | 900 nmol/kg/d | 9000 nmol/kg/d |
|---|---|---|---|---|
| TG (mg/dL) | 29.6 ± 5.9 | 19.4 ± 2.2 (↓ 34%) | 18.4 ± 2.3 (↓ 38%) | 22.0 ± 2.2 (↓ 26%) |

Example 23

Effect of Enho 1 on Weight Loss

The effect of Enho-1 upon weight loss was tested over the course of 7 days using DIO C57BL/6J mice (Charles River Laboratories). The mice were fed a high fat diet (Research Diets 12492) for 10 weeks prior to the start of the experiment, which was begun when the mice were 15-16 weeks of age. Control mice received vehicle only while test mice each received doses of either 90 nmol/kg/d, 900 nmol/kg/d or 9000 nmol/kg/d. The injections were given as 3 ip injections at 0800, 1200 and 1600 h for 7 days. On day 8, the mice were given the 0800 h injection and were sacrificed 1-3 h later.

The eight control mice exhibited mean pre- and post-treatment weights of 34.2 g (SE±1.5 g) and 32.6 g (SE±1.0), respectively, representing a 4.5% (SE±1.5) reduction in total body weight.

Eight test mice receiving 90 nmol/kg/d Enho 1 exhibited mean pre- and post-treatment weights of 36.5 g (SE±1.3) and 34.0 g (SD±0.9), respectively, representing a 6.6% (SE±1.1) reduction in total body weight.

Seven test mice receiving 900 nmol/kg/d Enho 1 exhibited mean pre- and post-treatment weights of 37.9 g (SE±1.4) and 36.0 g (SE±1.2), respectively, representing a 7.1% (SE±1.2) reduction in total body weight.

Lastly, seven test mice receiving 9000 nmol/kg/d Enho 1 exhibited mean pre- and post-treatment weights of 33.8 g (SE±10.8) and 31.6 g (SE±0.7), respectively, representing a 6.7% (SE±1.3) reduction in total body weight.

These results are reported in Table 13.

TABLE 13

The effect of Enho-1 upon weight loss

|  | Control | 90 nmol/kg/d | 900 nmol/kg/d | 9000 nmol/kg/d |
|---|---|---|---|---|
| Weight (pre-treatment) | 34.2 ± 1.5 | 36.5 ± 1.3 | 37.9 ± 1.4 | 33.8 ± 0.8 |
| Weight (termination) | 32.6 ± 1.0 | 34.0 ± 1.0 | 36.0 ± 1.2 | 31.6 ± 0.7 |
| Delta body weight |  |  |  |  |
| Grams | −1.6 ± 0.6 | −2.5 ± 0.4 | −2.8 ± 0.6 | −2.3 ± 0.5 |
| % | −4.5 ± 1.5 | −6.6 ± 1.1 | −7.1 ± 1.2 | −6.7 ± 1.3 |

Example 24

Effect of Enho 1 on Insulin and Glucose

The effect of Enho-1 upon insulin and glucose was tested over the course of 7 days using DIO C57BL/6J mice (Charles River Laboratories). The mice were fed a high fat diet (Research Diets 12492) for 10 weeks prior to the start of the experiment, which was begun when the mice were 15-16 weeks of age. Control mice received vehicle only while test mice each received doses of either 90 nmol/kg/d, 900 nmol/kg/d or 9000 nmol/kg/d. The injections were given as 3 ip injections at 0800, 1200 and 1600 h for 7 days. On day 8, the mice were given the 0800 h injection and were sacrificed 1-3 h later at which time blood samples were collected and levels of insulin and glucose determined.

The HOMA-IR for each treatment was calculated using the following formula:

$$((\text{glucose mg/dL} \div 18) \times (\text{insulin ng/ml} \times 25.05)) \div 22.5$$

Eight control mice demonstrated a post-test mean blood glucose level of 191 mg/dL (SE±10) and an insulin level of 1.9 ng/ml (SE±0.3); the HOMA-IR value for the control group was determined to be 22 (SE±4).

The eight test mice which received 90 nmol/kg/d of Enho 1 demonstrated a post-test mean blood glucose level of 182 mg/dL (SE±17) and an insulin level of 1.3 ng/ml (SE±0.1); the HOMA-IR value for this group was determined to be 15 (SE±2), representing a decrease of 15% as compared to the control group.

The seven test mice which received 900 nmol/kg/d of Enho 1 demonstrated a post-test mean blood glucose level of 212 mg/dL (SE±11) and an insulin level of 2.2 ng/ml (SE±0.3); the HOMA-IR value for this group was determined to be 29 (SE±4), representing a decrease of 29% (p<0.02) as compared to the control group.

The seven test mice which received 9000 nmol/kg/d of Enho 1 demonstrated a post-test mean blood glucose level of 190 mg/dL (SE±16) and an insulin level of 1.3 ng/ml (SE±0.2); the HOMA-IR value for this group was determined to be 16 (SE±4), representing a decrease of 27 as compared to the control group.

These results are reported in Table 14.

TABLE 14

The effect of Enho-1 upon insulin and glucose

|  | Control | 90 nmol/kg/d | 900 nmol/kg/d | 9000 nmol/kg/d |
|---|---|---|---|---|
| Blood glucose (mg/dL) | 191 ± 10 | 182 ± 17 | 212 ± 11 | 190 ± 16 |
| Insulin (ng/ml) | 1.9 ± 0.3 | 1.3 ± 0.1 | 2.2 ± 0.3 | 1.3 ± 0.2 |
| HOMA-IR | 22 ± 4 | 15 ± 2 (↓ 32%) | 29 ± 4 | 16 ± 4 (↓ 27%) |

Example 25

Effect of Enho 1 on Blood Lipids

The effect of Enho-1 upon levels of blood lipids was tested over the course of 7 days using DIO C57BL/6J mice (Charles River Laboratories). The mice were fed a high fat diet (Research Diets 12492) for 10 weeks prior to the start of the experiment, which was begun when the mice were 15-16 weeks of age. Control mice received vehicle only while test mice each received doses of either 90 nmol/kg/d, 900 nmol/kg/d or 9000 nmol/kg/d. The injections were given as 3 ip injections at 0800, 1200 and 1600 h for 7 days. On day 8, the mice were given the 0800 h injection and were sacrificed 1-3 h later at which time blood samples were collected and levels of trigylcerides determined. Triglycerides were measured using a Triglyceride L-Type TG H kit (Wako Diagnostics).

Eight control mice exhibited a mean blood triglyceride level of 22.9 mg/dL (SE±2.8).

Eight test mice which received 90 nmol/kg/d of Enho 1 demonstrated a post-test blood TG level of 22.5 mg/dL (SE±6.0).

Seven test mice which received 900 nmol/kg/d of Enho 1 demonstrated a post-test blood TG level of 38.0 mg/dL (SE±12.5).

The final group of seven mice which received 9000 nmol/kg/d of Enho 1 demonstrated a post-test blood TG level of 18.5 mg/dL (SE±1.7), a decrease of 19% from the control.

These results are reported in Table 15.

TABLE 15

The effect of Enho-1 upon levels of blood lipids

|  | Control | 90 nmol/kg/d | 900 nmol/kg/d | 9000 nmol/kg/d |
|---|---|---|---|---|
| TG (mg/dL) | 22.9 ± 2.8 | 22.5 ± 6.0 | 38.0 ± 12.5 | 18.5 ± 1.7 (↓ 19%) |

Miscellaneous

An "effective amount" of a Enho1 protein or peptide is an amount that decreases the level of insulin resistance or of dyslipidemia, or that prevents, delays or reduces the incidence of the onset of type 2 diabetes in obese insulin resistant patients by a statistically significant degree. "Statistical significance" is determined as the $P<0.05$ level, or by such other measure of statistical significance as is commonly used in the art for a particular type of experimental determination.

The term "Enho1" used herein and in the claims refers to the protein Enho1 (SEQ.ID.NO. 2), its functional peptides (e.g., Enho1$^{34-76}$), derivatives and analogs. The terms "derivatives" and "analogs" are understood to be proteins that are similar in structure to Enho1 and that exhibit a qualitatively similar effect to the unmodified Enho1. The term "functional peptide" refers to a piece of the Enho1 protein that still binds to the Enho1 receptor or is able to activate changes inside body cells, e.g., adipocytes or hepatocytes.

The administration of Enho1, its functional peptides, its analogs and derivatives in accordance with the present invention may be used to reverse insulin resistance and dyslipidemia, to delay onset to type 2 diabetes in obese insulin resistant subjects, and to prevent or delay onset of obesity. These compounds can also be used as therapeutic or diagnostic agents for hypercholesterolemia, hypertriglyceridemia, insulin resistance, obesity, and diabetes.

The term "therapeutically effective amount" as used herein refers to an amount of Enho1 protein, a fragment, or a derivative or analog sufficient either increase body energy expenditure, decrease serum triglyceride, decrease serum cholesterol, decrease hyperlipidemia, or decrease insulin resistance to a statistically significant degree ($p<0.05$). The dosage ranges for the administration of Enho1 protein are those that produce the desired effect. Generally, the dosage will vary with the age, weight, condition, sex of the patient. A person of ordinary skill in the art, given the teachings of the present specification, may readily determine suitable dosage ranges. The dosage can be adjusted by the individual physician in the event of any contraindications. In any event, the effectiveness of treatment can be determined by monitoring either the body metabolism, body weight, or the serum glucose, triglyceride, cholesterol levels by methods well known to those in the field. Moreover, Enho1 can be applied in pharmaceutically acceptable carriers known in the art.

This method of treatment may be used in vertebrates generally, including human and non-human mammals. Peptides in accordance with the present invention may be administered to a patient by any suitable means, including oral, intravenous, parenteral, subcutaneous, intrapulmonary, and intranasal administration.

Parenteral infusions include intramuscular, intravenous, intraarterial, or intraperitoneal administration. The compound may also be administered transdermally, for example in the form of a slow-release subcutaneous implant, or orally in the form of capsules, powders, or granules. It may also be administered by inhalation.

Pharmaceutically acceptable carrier preparations for parenteral administration include sterile, aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. The active therapeutic ingredient may be mixed with excipients that are pharmaceutically acceptable and are compatible with the active ingredient. Suitable excipients include water, saline, dextrose, glycerol and ethanol, or combinations thereof. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, inert gases, and the like.

The form may vary depending upon the route of administration. For example, compositions for injection may be provided in the form of an ampule, each containing a unit dose amount, or in the form of a container containing multiple doses.

The compound may be formulated into therapeutic compositions as pharmaceutically acceptable salts. These salts include acid addition salts formed with inorganic acids, for example hydrochloric or phosphoric acid, or organic acids such as acetic, oxalic, or tartaric acid, and the like. Salts also include those formed from inorganic bases such as, for example, sodium, potassium, ammonium, calcium or ferric hydroxides, and organic bases such as isopropylamine, trimethylamine, histidine, procaine and the like. The compositions may be administered intravenously, subcutaneously, intramuscularly.

Controlled delivery may be achieved by admixing the active ingredient with appropriate macromolecules, for example, polyesters, polyamino acids, polyvinyl pyrrolidone, ethylenevinylacetate, methylcellulose, carboxymethylcellulose, prolamine sulfate, or lactide/glycolide copolymers. The rate of release of the active compound may be controlled by altering the concentration of the macromolecule.

Another method for controlling the duration of action comprises incorporating the active compound into particles of a polymeric substance such as a polyester, peptide, hydrogel, polylactide/glycolide copolymer, or ethylenevinylacetate copolymers. Alternatively, an active compound may be encapsulated in microcapsules prepared, for example, by coacervation techniques or by interfacial polymerization, for example, by the use of hydroxymethylcellulose or gelatin-microcapsules or poly(methylmethacrylate) microcapsules, respectively, or in a colloid drug delivery system. Colloidal dispersion systems include macromolecule complexes, nanocapsules, microspheres, beads, and lipid-based systems including oil-in-water emulsions, micelles, mixed micelles, and liposomes.

In addition, all or portions of the nucleic acid sequence (SEQ ID NO:1) (e.g., the open reading frame underlined in FIG. 4) can be used to make plasmids or vectors to incorporate the Enho1 gene into organisms to increase the production of the Enho1 protein. It will be understood by those skilled in the art that the nucleic acid sequence of SEQ ID NO:1 is not the only sequence that can be used to produce the Enho1 protein. Also contemplated are those nucleic acid sequences that encode identical proteins but that, because of the degeneracy of the genetic code, possess different nucleotide sequences. The genetic code may be found in numerous references concerning genetics or biology, including, for example, FIG. 9.1 on page 214 of B. Lewin, *Genes VI* (Oxford University Press, New York, 1997). FIG. 9.3 on page 216 of Lewin directly illustrates the degeneracy of the genetic code. For example, the codon for asparagine may be AAT or AAC.

The invention also encompasses nucleotide sequences encoding Enho1 proteins having one or more silent amino acid changes in portions of the molecule not involved with receptor binding or protein secretion. For example, alterations in the nucleotide sequence that result in the production of a chemically equivalent amino acid at a given site are contemplated; thus, a codon for the amino acid alanine, a hydrophobic amino acid, may be substituted by a codon encoding another hydrophobic residue, such as glycine, or may be substituted with a more hydrophobic residue such as valine, leucine, or isoleucine. Similarly, changes that result in the substitution of one negatively-charged residue for another, such as aspartic acid for glutamic acid, or one positively-charged residue for another, such as lysine for arginine, can also be expected to produce a biologically equivalent product. See, e.g., FIG. 1.8 on page 10 of Lewin (1997), showing the nature of the side chains of the "standard" 20 amino acids encoded by the genetic code. (Note also a typographical error in that published figure, namely that the abbreviation for glutamine should be "Gln.")

REFERENCES

1. Gunning, P., Leavitt, J., Muscat, G., Ng, S. Y. & Kedes, L. (1987) A human beta-actin expression vector system directs high-level accumulation of antisense transcripts. Proc Natl Acad Sci USA 84: 4831-4835.
2. Reaven, G. M. (1995) Pathophysiology of insulin resistance in human disease. Physiol Rev 75: 473-486.
3. Horton, J. D., Goldstein, J. L. & Brown, M. S. (2002) SREBPs: activators of the complete program of cholesterol and fatty acid synthesis in the liver. J Clin Invest 109: 1125-1131.
4. Shimomura, I., Matsuda, M., Hammer, R. E., Bashmakov, Y., Brown, M. S. & Goldstein, J. L. (2000) Decreased IRS-2 and increased SREBP-1c lead to mixed insulin resistance and sensitivity in livers of lipodystrophic and ob/ob mice. Mol Cell 6: 77-86.
5. Gavrilova, O., Haluzik, M., Matsusue, K., Cutson, J. J., Johnson, L., Dietz, K. R., Nicol, C., Vinson, C., Gonzalez, F. & Reitman, M. L. (2003) Liver PPARgamma contributes to hepatic steatosis, triglyceride clearance, and regulation of body fat mass. J Biol Chem.
6. Matsusue, K., Haluzik, M., Lambert, G., Yim, S. H., Gavrilova, O., Ward, J. M., Brewer, B., Jr., Reitman, M. L. & Gonzalez, F. J. (2003) Liver-specific disruption of PPARgamma in leptin-deficient mice improves fatty liver but aggravates diabetic phenotypes. J Clin Invest 111: 737-747.
7. Yahagi, N., Shimano, H., Hasty, A. H., Matsuzaka, T., Ide, T., Yoshikawa, T., Amemiya-Kudo, M., Tomita, S., Okazaki, H. et al. (2002) Absence of sterol regulatory element-binding protein-1 (SREBP-1) ameliorates fatty livers but not obesity or insulin resistance in Lep(ob)/Lep(ob) mice. J Biol Chem 277: 19353-19357.
8. Araki, E., Lipes, M. A., Patti, M. E., Bruning, J. C., Haag, B., 3rd, Johnson, R. S. & Kahn, C. R. (1994) Alternative pathway of insulin signalling in mice with targeted disruption of the IRS-1 gene. Nature 372: 186-190.
9. Withers, D. J., Gutierrez, J. S., Towery, H., Burks, D. J., Ren, J. M., Previs, S., Zhang, Y., Bernal, D., Pons, S. et al. (1998) Disruption of IRS-2 causes type 2 diabetes in mice. Nature 391: 900-904.
10. Kido, Y., Burks, D. J., Withers, D., Bruning, J. C., Kahn, C. R., White, M. F. & Accili, D. (2000) Tissue-specific insulin resistance in mice with mutations in the insulin receptor, IRS-1, and IRS-2. J Clin Invest 105: 199-205.
11. Previs, S. F., Withers, D. J., Ren, J. M., White, M. F. & Shulman, G. I. (2000) Contrasting effects of IRS-1 versus IRS-2 gene disruption on carbohydrate and lipid metabolism in vivo. J Biol Chem 275: 38990-38994.
12. White, M. F. (2002) IRS proteins and the common path to diabetes. Am J Physiol Endocrinol Metab 283: E413-422.
13. Ravussin, E. & Smith, S. R. (2002) Increased fat intake, impaired fat oxidation, and failure of fat cell proliferation result in ectopic fat storage, insulin resistance, and type 2 diabetes mellitus. Ann N Y Acad Sci 967: 363-378.
14. Lowell, B. B. & Shulman, G. I. (2005) Mitochondrial dysfunction and type 2 diabetes. Science 307: 384-387.
15. Sutton, G. M., Trevaskis, J. L., Hulver, M. W., McMillan, R. P., Markward, N. J., Babin, M. J., Meyer, E. A. & Butler, A. A. (2006) Diet-genotype interactions in the development of the obese, insulin-resistant phenotype of C57BL/6J mice lacking melanocortin-3 or -4 receptors. Endocrinology 147: 2183-2196.
16. Elmquist, J. K., Coppari, R., Balthasar, N., Ichinose, M. & Lowell, B. B. (2005) Identifying hypothalamic pathways controlling food intake, body weight, and glucose homeostasis. J Comp Neurol 493: 63-71.
17. Asilmaz, E., Cohen, P., Miyazaki, M., Dobrzyn, P., Ueki, K., Fayzikhodjaeva, G., Soukas, A. A., Kahn, C. R., Ntambi, J. M. et al. (2004) Site and mechanism of leptin action in a rodent form of congenital lipodystrophy. J Clin Invest 113: 414-424.
18. Morton, G. J., Blevins, J. E., Williams, D. L., Niswender, K. D., Gelling, R. W., Rhodes, C. J., Baskin, D. G. & Schwartz, M. W. (2005) Leptin action in the forebrain regulates the hindbrain response to satiety signals. J Clin Invest 115: 703-710.
19. Coppari, R., Ichinose, M., Lee, C. E., Pullen, A. E., Kenny, C. D., McGovern, R. A., Tang, V., Liu, S. M., Ludwig, T. et al. (2005) The hypothalamic arcuate nucleus: A key site for mediating leptin's effects on glucose homeostasis and locomotor activity. Cell Metabolism 1: 63-72.
20. Minokoshi, Y., Kim, Y.-B., Peroni, O. D., Fryer, L. G. D., Muller, C., Carling, D. & Kahn, B. B. (2002) Leptin stimulates fatty-acid oxidation by activating AMP-activated protein kinase. Nature 415: 339-343.
21. Roden, M., Price, T. B., Perseghin, G., Petersen, K. F., Rothman, D. L., Cline, G. W. & Shulman, G. I. (1996) Mechanism of free fatty acid-induced insulin resistance in humans. J Clin Invest 97: 2859-2865.
22. Dresner, A., Laurent, D., Marcucci, M., Griffin, M. E., Dufour, S., Cline, G. W., Slezak, L. A., Andersen, D. K., Hundal, R. S. et al. (1999) Effects of free fatty acids on glucose transport and IRS-1-associated phosphatidylinositol 3-kinase activity. J Clin Invest 103: 253-259.

23. Kim, Y. B., Shulman, G. I. & Kahn, B. B. (2002) Fatty acid infusion selectively impairs insulin action on Akt1 and protein kinase C lambda/zeta but not on glycogen synthase kinase-3. J Biol Chem 277: 32915-32922.
24. Roden, M., Krssak, M., Stingl, H., Gruber, S., Hofer, A., Furnsinn, C., Moser, E. & Waldhausl, W. (1999) Rapid impairment of skeletal muscle glucose transport/phosphorylation by free fatty acids in humans. Diabetes 48: 358-364.
25. Yu, C., Chen, Y., Cline, G. W., Zhang, D., Zong, H., Wang, Y., Bergeron, R., Kim, J. K., Cushman, S. W. et al. (2002) Mechanism by which fatty acids inhibit insulin activation of insulin receptor substrate-1 (IRS-1)-associated phosphatidylinositol 3-kinase activity in muscle. J Biol Chem 277: 50230-50236.
26. Rajala, M. W. & Scherer, P. E. (2003) Minireview: The adipocyte—at the crossroads of energy homeostasis, inflammation, and atherosclerosis. Endocrinology 144: 3765-3773.
27. Kadowaki, T. & Yamauchi, T. (2005) Adiponectin and adiponectin receptors. Endocr Rev 26: 439-451.
28. Flier, J. S. (2004) Obesity wars. Molecular progress confronts an expanding epidemic. Cell 116: 337-350.
29. Nishizawa, H., Matsuda, M., Yamada, Y., Kawai, K., Suzuki, E., Makishima, M., Kitamura, T. & Shimomura, I. (2004) Musclin, a novel skeletal muscle-derived secretory factor. J Biol Chem 279: 19391-19395.
30. Oike, Y., Akao, M., Yasunaga, K., Yamauchi, T., Morisada, T., Ito, Y., Urano, T., Kimura, Y., Kubota, Y. et al. (2005) Angiopoietin-related growth factor antagonizes obesity and insulin resistance. Nat Med 11: 400-408.
31. Sutton, G. M., Trevaskis, J. L., Hulver, M. W., MacMillan, R. P., Markward, N. J., Meyer, E. A., Babin, M. J. & Butler, A. A. (2006) Diet-Genotype Interactions in the Development of the Obese, Insulin Resistant Phenotype of C57BL/6J mice lacking Melanocortin-3 or -4 Receptors. Endocrinology 147: 2183-2196.
32. Albarado, D. C., McClaine, J., Stephens, J. M., Mynatt, R. L., Ye, J., Bannon, A. W., Richards, W. G. & Butler, A. A. (2004) Impaired coordination of nutrient intake and substrate oxidation in melanocortin-4 receptor knockout mice. Endocrinology 145: 243-252.
33. Browning, J. D. & Horton, J. D. (2004) Molecular mediators of hepatic steatosis and liver injury. J Clin Invest 114: 147-152.
34. Sparks, L. M., Xie, H., Koza, R. A., Mynatt, R., Hulver, M. W., Bray, G. A. & Smith, S. R. (2005) A high-fat diet coordinately downregulates genes required for mitochondrial oxidative phosphorylation in skeletal muscle. Diabetes 54: 1926-1933.
35. Teran-Garcia, M., Rankinen, T., Koza, R. A., Rao, D. C. & Bouchard, C. (2005) Endurance training-induced changes in insulin sensitivity and gene expression. Am J Physiol Endocrinol Metab 288: E1168-1178.
36. Koza, R. A., Nikonova, L., Hogan, J., Rim, J. S., Mendoza, T., Faulk, C., Skaf, J. & Kozak, L. P. (2006) Changes in gene expression foreshadow diet-induced obesity in genetically identical mice. PLoS Genet 2: e81.
37. Clark, H. F., Gurney, A. L., Abaya, E., Baker, K., Baldwin, D., Brush, J., Chen, J., Chow, B., Chui, C. et al. (2003) The secreted protein discovery initiative (SPDI), a large-scale effort to identify novel human secreted and transmembrane proteins: a bioinformatics assessment. Genome Res 13: 2265-2270.
38. Kay, M. A., Glorioso, J. C. & Naldini, L. (2001) Viral vectors for gene therapy: the art of turning infectious agents into vehicles of therapeutics. Nat Med 7: 33-40.
39. Chen, G., Koyama, K., Yuan, X., Lee, Y., Zhou, Y. T., O'Doherty, R., Newgard, C. B. & Unger, R. H. (1996) Disappearance of body fat in normal rats induced by adenovirus-mediated leptin gene therapy. Proc Natl Acad Sci USA 93: 14795-14799.
40. Satoh, H., Nguyen, M. T., Trujillo, M., Imamura, T., Usui, I., Scherer, P. E. & Olefsky, J. M. (2005) Adenovirus-mediated adiponectin expression augments skeletal muscle insulin sensitivity in male Wistar rats. Diabetes 54: 1304-1313.
41. Satoh, H., Nguyen, M. T., Miles, P. D., Imamura, T., Usui, I. & Olefsky, J. M. (2004) Adenovirus-mediated chronic "hyper-resistinemia" leads to in vivo insulin resistance in normal rats. J Clin Invest 114: 224-231.
42. Xu, A., Wang, Y., Keshaw, H., Xu, L. Y., Lam, K. S. & Cooper, G. J. (2003) The fat-derived hormone adiponectin alleviates alcoholic and nonalcoholic fatty liver diseases in mice. J Clin Invest 112: 91-100.
43. Yamauchi, T., Kamon, J., Minokoshi, Y., Ito, Y., Waki, H., Uchida, S., Yamashita, S., Noda, M., Kita, S. et al. (2002) Adiponectin stimulates glucose utilization and fatty-acid oxidation by activating AMP-activated protein kinase. Nat Med 8: 1288-1295.
44. George, S., Rochford, J. J., Wolfrum, C., Gray, S. L., Schinner, S., Wilson, J. C., Soos, M. A., Murgatroyd, P. R., Williams, R. M. et al. (2004) A family with severe insulin resistance and diabetes due to a mutation in AKT2. Science 304: 1325-1328.
45. Bae, S. S., Cho, H., Mu, J. & Birnbaum, M. J. (2003) Isoform-specific regulation of insulin-dependent glucose uptake by Akt/protein kinase B. J Biol Chem 278: 49530-49536.
46. Trevaskis, J. L. & Butler, A. A. (2005) Double leptin (Lepob) and melanocortin-4 receptor (Mc4r) gene mutations have an additive effect on fat mass, and are associated with reduced effects of leptin on weight loss and food intake. Endocrinology 146: 4257-4265.
47. Clegg, D. J., Brown, L. M., Woods, S. C. & Benoit, S. C. (2006) Gonadal hormones determine sensitivity to central leptin and insulin. Diabetes 55: 978-987.
48. Clegg, D. J., Riedy, C. A., Smith, K. A., Benoit, S. C. & Woods, S. C. (2003) Differential sensitivity to central leptin and insulin in male and female rats. Diabetes 52: 682-687.
49. Butler, A. A., Blakesley, V. A., Koval, A., deJong, R., Groffen, J. & LeRoith, D. (1997) In vivo regulation of CrkII and CrkL proto-oncogenes in the uterus by insulin-like growth factor-I. Differential effects on tyrosine phosphorylation and association with paxillin. J Biol Chem 272: 27660-27664.
50. Butler, A. A. (2006) The melanocortin system and energy balance. Peptides 27: 301-309.
51. Aizawa-Abe, M., Ogawa, Y., Masuzaki, H., Ebihara, K., Satoh, N., Iwai, H., Matsuoka, N., Hayashi, T., Hosoda, K. et al. (2000) Pathophysiological role of leptin in obesity-related hypertension. J Clin Invest 105: 1243-1252.
52. Ogawa, Y., Masuzaki, H., Hosoda, K., Aizawa-Abe, M., Suga, J., Suda, M., Ebihara, K., Iwai, H., Matsuoka, N. et al. (1999) Increased glucose metabolism and insulin sensitivity in transgenic skinny mice overexpressing leptin. Diabetes 48: 1822-1829.
53. Combs, T. P., Pajvani, U. B., Berg, A. H., Lin, Y., Jelicks, L. A., Laplante, M., Nawrocki, A. R., Rajala, M. W., Parlow, A. F. et al. (2004) A transgenic mouse with a deletion in the collagenous domain of adiponectin displays elevated circulating adiponectin and improved insulin sensitivity. Endocrinology 145: 367-383.

54. Yamauchi, T., Kamon, J., Waki, H., Imai, Y., Shimozawa, N., Hioki, K., Uchida, S., Ito, Y., Takakuwa, K. et al. (2003) Globular adiponectin protected ob/ob mice from diabetes and ApoE-deficient mice from atherosclerosis. J Biol Chem 278: 2461-2468.
55. Collins, S., Martin, T. L., Surwit, R. S. & Robidoux, J. (2004) Genetic vulnerability to diet-induced obesity in the C57BL/6J mouse: physiological and molecular characteristics. Physiol Behav 81: 243-248.
56. Bates, S. H., Kulkarni, R. N., Seifert, M. & Myers, M. G., Jr. (2005) Roles for leptin receptor/STAT3-dependent and -independent signals in the regulation of glucose homeostasis. Cell Metab 1: 169-178.
57. Shimomura, I., Bashmakov, Y. & Horton, J. D. (1999) Increased levels of nuclear SREBP-1c associated with fatty livers in two mouse models of diabetes mellitus. J Biol Chem 274: 30028-30032.
58. Masuzaki, H., Ogawa, Y., Aizawa-Abe, M., Hosoda, K., Suga, J., Ebihara, K., Satoh, N., Iwai, H., Inoue, G. et al. (1999) Glucose metabolism and insulin sensitivity in transgenic mice overexpressing leptin with lethal yellow agouti mutation: usefulness of leptin for the treatment of obesity-associated diabetes. Diabetes 48: 1615-1622.
59. Heisler, L. K., Jobst, E. E., Sutton, G. M., Zhou, L., Borok, E., Thornton-Jones, Z., Liu, H. Y., Zigman, J. M., Balthasar, N. et al. (2006) Serotonin Reciprocally Regulates Melanocortin Neurons to Modulate Food Intake. Neuron-Jul 20; 51(2):239-249.
60. Butler, A. A., Kesterson, R. A., Khong, K., Cullen, M. J., Pelleymounter, M. A., Dekoning, J., Baetscher, M. & Cone, R. D. (2000) A unique metabolic syndrome causes obesity in the melanocortin-3 receptor-deficient mouse. Endocrinology 141: 3518-3521.

The complete disclosures of all references cited in this specification are hereby incorporated by reference. In the event of an otherwise irreconcilable conflict, however, the present specification shall control.

What is claimed:

1. A method for decreasing symptoms of a pathophysiology relating to homeostasis of body mass, comprising administering to a subject a therapeutically effective amount of a pharmaceutical composition comprising a Enho1 peptide or an Enho1 peptide fragment, wherein said peptide or fragment is selected from the group consisting of the sequences set forth in SEQ ID NOS: 10, 11, 14, 15, and 17; and wherein said symptoms are one or more symptoms selected from the group consisting of hyperglycemia, insulin resistance, hyperinsulinemia, hepatic steatosis, hyperlipidemia, increased cholesterol, and increased triglycerides.

2. A method according to claim 1, additionally comprising administering to a subject a compound selected from the group consisting of leptin and adiponectin.

3. A method according to claim 1, wherein the step of administering to a subject comprises intraperitoneal administration.

* * * * *